US009723817B2

(12) United States Patent
Lockery

(10) Patent No.: US 9,723,817 B2
(45) Date of Patent: Aug. 8, 2017

(54) ELECTROPHARYNGEOGRAM ARRAYS AND METHODS OF USE

(71) Applicant: The State of Oregon Acting by and through the State Board of Higher Education on behalf of the University of Oregon, Eugene, OR (US)

(72) Inventor: Shawn Lockery, Eugene, OR (US)

(73) Assignee: State of Oregon Acting by and through the State Board of Higher Education on behalf of the University of Oregon, Eugene, OR (US)

( * ) Notice: Subject to any disclaimer, the term of this patent is extended or adjusted under 35 U.S.C. 154(b) by 1118 days.

(21) Appl. No.: 13/673,611

(22) Filed: Nov. 9, 2012

(65) Prior Publication Data

US 2013/0118411 A1 May 16, 2013

Related U.S. Application Data

(60) Provisional application No. 61/558,249, filed on Nov. 10, 2011.

(51) Int. Cl.
| | | |
|---|---|---|
| *A01K 29/00* | (2006.01) | |
| *A01K 67/033* | (2006.01) | |
| *G01N 27/02* | (2006.01) | |
| *G01N 33/50* | (2006.01) | |

(52) U.S. Cl.
CPC .......... *A01K 29/005* (2013.01); *A01K 67/033* (2013.01); *G01N 27/02* (2013.01); *G01N 33/5085* (2013.01); *G01N 2333/43534* (2013.01)

(58) Field of Classification Search
CPC ............................... A01K 29/00; A01K 67/033
See application file for complete search history.

(56) References Cited

U.S. PATENT DOCUMENTS

| | | | |
|---|---|---|---|
| 7,030,290 | B2 | 4/2006 | Verwaerde et al. |
| 7,083,947 | B2 | 8/2006 | Verwaerde et al. |
| 7,751,048 | B2 | 7/2010 | Yang et al. |
| 7,982,883 | B2 | 7/2011 | Cui et al. |
| 2010/0263599 | A1 | 10/2010 | Yanik et al. |
| 2012/0061240 | A1* | 3/2012 | Selvaganapathy et al. .. 204/451 |

OTHER PUBLICATIONS

S. Elizabeth et al. Lifespan-on a chip: microfluidic chambers for performing lifelong observation of C. elegans, Lab Chip, 2010, 10, 589-597.*

S. Elizabeth Hulme et al., Lifespan-on-a chip: microfluidic chambers for performing lifelong observation of C. elegans, Lab Chip, 2010, 10, 589-597.*
Heyu Li et al. Identification of Chemical Synapases in the pharynx of Caenorhabditis elegans, Proc. Natl. Acad. Sci. USA, vol. 94, 5912-5916, 1997.*
Avery et al., "Electrophysiological Methods," *Methods in Cell Biology*, vol. 48, pp. 251-269, 1995.
Chronis et al, "Microfluidics for in vivo Imaging of Neuronal and Behavioral Activity in *Caenorhabditis elegans,*" *Nature Methods*, vol. 4, No. 9, pp. 727-731, 2007.
Chung et al., "Automated On-Chip Rapid Microscopy, Phenotyping and Sorting of *C. elegans,*" *Nature Methods*, vol. 5, No. 7, pp. 637-643, 2008.
Faumont et al., "An Image-Free Opto-Mechanical System for Creating Virtual Environments and Imaging Neuronal Activity in Freely Moving *Caenorhabditis elegans,*" *PLoS ONE*, vol. 6, No. 9, e24666, 2011 (12 pages).
Hulme et al, "A Microfabricated Array of Clamps for Immobilizing and Imaging *C. elegans,*" *Lab Chip*, vol. 7, pp. 1515-1523, 2007.
Hulme et al., "Microfluidics: Streamlining Discovery in Worm Biology," *Nature Methods*, vol. 5, No. 7, pp. 589-590, 2008.
Hulme et al., "Lifespan-on-a-chip: Microfluidic Chambers for Performing Lifelong Observation of *C. elegans,*" *Lab Chip*, vol. 10, pp. 589-597, 2010.
Lockery, "Channeling the Worm: Microfluidic Devices for Nematode Neurobiology," *Nature Methods*, vol. 4, No. 9, pp. 691-692, 2007.
Lockery et al, "Artificial Dirt: Microfluidic Substrates for Nematode Neurobiology and Behavior," *Journal of Neurophysiol.*, vol. 99, pp. 3136-3143, 2008.
Lockery et al., "A microfluidic device for whole-animal screening using electrophysiological measures in the nematode *C. elegans,*" *Lab Chip* vol. 12, pp. 2211-2220, 2012.
Fuerstman et al., "The pressure drop along rectangular microchannels containing bubbles," *Lab Chip*, vol. 7, pp. 1479-1489, 2007.
Raizen et al., "Electrical Activity and Behavior in the Pharynx of Caenorhabditis elegans," *Neuron*, vol. 12, No. 3, pp. 483-492, 1994.

* cited by examiner

*Primary Examiner* — Michael G Hartley
*Assistant Examiner* — Jagadishwar Samala
(74) *Attorney, Agent, or Firm* — Klarquist Sparkman, LLP

(57) ABSTRACT

Disclosed herein are devices, systems, and methods for measuring an electropharyngeogram (EPG) in living organisms. In some embodiments, the devices and systems disclosed herein include an array for sorting and immobilizing an organism (such as a nematode) for measurement of an EPG and/or optical imaging. Also disclosed are methods for identifying therapeutic or toxic compounds utilizing the disclosed devices and systems. In some embodiments, the methods include screening for compounds with anthelmintic activity, toxicity (for example HERG channel blockers), or candidate drugs for treatment of a variety of human and/or animal diseases.

17 Claims, 12 Drawing Sheets

2 s

ELECTROPHARYNGEOGRAM ARRAYS AND METHODS OF USE

CROSS REFERENCE TO RELATED APPLICATION

This claims the benefit of U.S. Provisional Application No. 61/558,249, filed Nov. 10, 2011, which is incorporated herein by reference in its entirety.

ACKNOWLEDGMENT OF GOVERNMENT SUPPORT

This invention was made with government support under 5RC1AI087059 awarded by the National Institutes of Health. The government has certain rights in the invention.

FIELD

This disclosure relates to devices and methods for measuring electropharyngeograms in an organism.

BACKGROUND

Nematodes are a major cause of disease in humans and economically important livestock species. Up to 30% of the world's population may be infected by parasitic worms, many of which are nematodes. The effects of nematode infection can be devastating, for example as in the case of river blindness (caused by infection with the nematode *Onchocerca volvulus*), in which juvenile nematodes invade the human cornea. Despite the high morbidity and mortality associated with nematode infection, anthelmintic drug discovery has been slow and has not kept pace with the emergence of anthelmintic resistant strains. Thus, there is a need for devices and methods for rapid and inexpensive screening for candidate anthelmintic drugs.

SUMMARY

Disclosed herein are devices (such as fluidic devices), systems, and methods for measuring an electropharyngeogram (EPG) in living organisms. In some embodiments, the devices and systems disclosed herein include an array for sorting and/or immobilizing one or more organisms (such as one or more nematodes) for measurement of an EPG and/or optical imaging.

Also disclosed are methods for identifying therapeutic or toxic compounds utilizing the disclosed devices and systems. In some embodiments, the methods include screening for compounds with anthelmintic activity, toxicity (for example HERG channel blockers), or candidate drugs for treatment of a variety of human and/or animal diseases.

The foregoing and other features of the disclosure will become more apparent from the following detailed description, which proceeds with reference to the accompanying figures.

BRIEF DESCRIPTION OF THE DRAWINGS

FIG. 4A is a set of EPG traces from the worms in control M9-5HT buffer 5 minutes before initiating drug perfusion. Voltage gains (Y axes) were adjusted to produce excursions of similar magnitudes.

FIG. 6A shows EPG in control M9-5HT buffer 30 minutes before drug perfusion. FIG. 6B is an EPG taken 10 minutes after perfusion of 10 mM levamisole in M9-5HT buffer. FIG. 6C is an EPG 60 minutes after resuming perfusion of control buffer (wash). The wash was initiated 40 minutes after onset of drug perfusion.

FIG. 7A shows a digital image of muscle cells of the terminal bulb of the pharynx and two additional muscle cells that express G-CaMP, a genetically targeted fluorescent probe for intracellular calcium concentration.

FIG. 9A shows an EPG from a wild type worm positioned in the EPG array without activation of the syringe pump (top). This produces a "loose" fit of the worm in the recording module (bottom).

DETAILED DESCRIPTION

I. Abbreviations

Figure 1A:
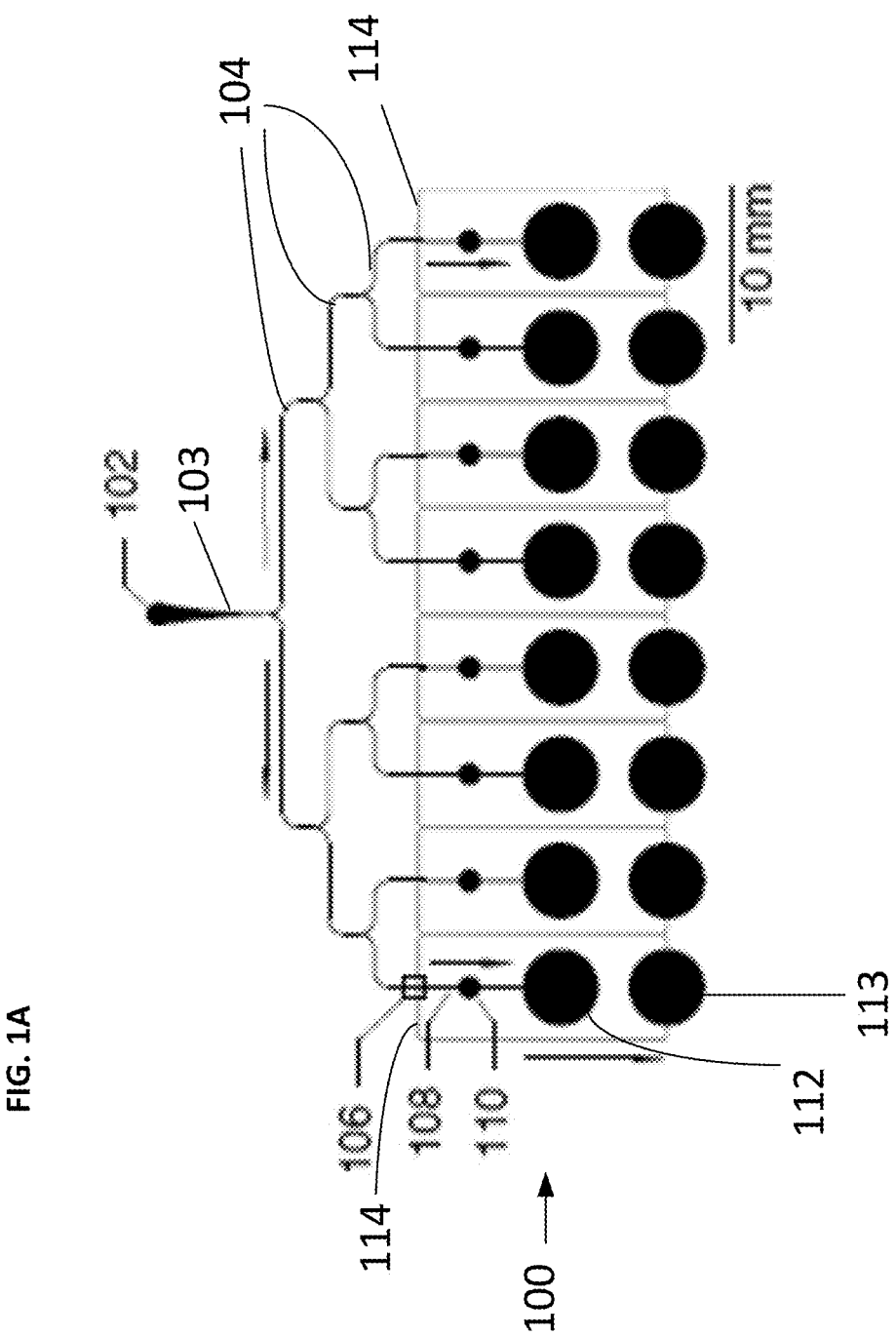
FIG. 1A is a top view of an exemplary 8-channel microfluidic device 100. The device includes an inlet port 102 connected to a series of distribution channels 104 which deliver worms or solutions to eight recording modules 106. The inlet port 102 includes a tapered area 103 connecting to the distribution channels 104. Each recording module 106 is connected to an electrode channel 108. Each electrode channel 108 contains an electrode port 110 into which a cylindrical metal electrode can be inserted during use. Each recording module is also connected to a pair of waste reservoirs 112 and 113. One waste reservoir 112 is connected to the electrode channel. The other waste reservoir 113 is connected to the vent channels 114 attached to each recording module. Direction of fluid flow is shown by arrows.

5HT serotonin
AChR acetylcholine receptor
DMSO dimethylsulfoxide
EPG electropharyngeogram
FPS frames per second
HERG human-ether-a-go-go-related gene or protein
IVM ivermectin
NGM nematode growth medium
PDMS poly(dimethyl siloxane)
SNR signal to noise ratio II. Terms Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. The term "comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); Robert A. Meyers (ed.), *Molecular Biology and Biotechnology: a Comprehensive Desk Reference*, published by VCH Publishers, Inc., 1995 (ISBN 1-56081-569-8); and King et al., *A Dictionary of Genetics*, 7$^{th}$ edition, published by Oxford University Press, 2006 (ISBN 0-19-530761-0).

In order to facilitate review of the various embodiments of the disclosure, the following explanations of specific terms are provided:

Anthelmintic (or Antihelminthic):

Compounds used to treat infection with parasitic worms, including roundworms (nematodes) and flatworms. Anthelmintics include, but are not limited to, six major classes of drugs. They include nicotinic acetylcholine receptor (AChR) agonists (such as levamisole), glutamate gated chloride channel agonists (such as ivermectin), nicotinic AChR antagonists (such as paraherquamide), SLO-1 potassium channel activators (such as emodepside), GABA receptor agonists (such as piperazine), and tubulin polymerization inhibitors (such as benzimidazoles).

Array:

An arrangement of biological samples or organisms ("features"), in addressable locations on or in a substrate. A "microarray" is an array that is miniaturized so as to require or be aided by microscopic examination for evaluation or analysis. Arrays are sometimes called chips or biochips. The array of features makes it possible to carry out a very large number of analyses at one time. The number of addressable locations on the array can vary, for example from at least one, to at least 2, to at least 5, to at least 10, to at least 20, to at least 30, to at least 50, to at least 75, to at least 100, or more. In particular examples, an array includes living organisms, such as a nematode (for example, *C. elegans*).

Within an array, each arrayed feature is addressable, in that its location can be reliably and consistently determined within at least two dimensions of the array. The feature location on an array can assume different shapes. For example, the array can be regular (such as arranged in uniform rows and columns) or irregular. Thus, in ordered arrays the location of each feature is assigned at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters).

*Caenorhabditis elegans:*

A free-living transparent nematode, about 1 mm in length, which lives in temperate soil environments. The basic anatomy of *C. elegans* includes a mouth, pharynx, intestine, gonad, and collagenous cuticle. *C. elegans* is widely used as a model organism for the study of developmental biology. It is a useful model organism because it is simple, easy to grow in bulk populations, and convenient for genetic analysis. In addition, *C. elegans* is one of the simplest organisms with a nervous system and the neurons have been completely mapped.

Channel:

A feature in or on an article (such as a disclosed device) that directs, at least partially, flow of a fluid. A channel can have any suitable cross-sectional shape, including, but not limited to circular, oval, square, or rectangular.

Contacting:

A state or condition of touching or being in immediate physical proximity, particularly direct physical association, for example both in solid form and/or in liquid form (for example, the placement of a test compound in contact with a cell or organism).

Electropharyngeogram (EPG):

Electrophysiological recording of the pumping activity of the pharynx of an organism (such as a nematode, for example, *C. elegans*). The EPG can be recorded non-invasively with surface electrodes. The waveform of the EPG approximates the derivative of the action potential waveform and includes the E or excitation phase (depolarization of the basal membranes of the pharyngeal muscle cells), the P or plateau phase (membrane potential remains depolarized and muscle contraction occurs), and the R or repolarization phase (return of membrane potential to negative values, muscle relaxation). The E phase includes two closely spaced positive spikes (the corpus and the terminal bulb contractions) and the R phase includes two negative spikes corresponding to relaxation of the corpus and the terminal bulb, respectively.

Fluidic Device:

A device that utilizes the flow of fluid to distribute substances and/or organisms (such as substances dissolved in a fluid and/or substances or organisms suspended in a fluid). A fluidic device can be of any dimension, so long as its dimensions are suitable to accommodate the size of substances or organisms included or suspended in the fluid.

In some examples, a device is a microfluidic device that exploits the properties of fluid flow that arise at length scales in the sub-millimeter range. One such property is laminar flow. In some examples, a microfluidic device has a channel or chamber with at least one dimension of 300 microns or less. In other examples, two dimensions are 300 microns or less. Some microfluidic devices are fabricated in glass whereas others are fabricated in a bio-compatible silicone elastomer by replica molding. The latter are referred to as soft-lithography microfluidic devices. The term "microfluidic device" is sometimes used as a synonym for the more general term "microfabricated device," which refers to an object that may or may not exploit the properties of fluid flow at the sub-millimeter scale.

Human Ether-a-go-go-Related (HERG):

Also known as potassium voltage-gated channel, subfamily H (eag-related), member 2 (KCNH2), long QT syndrome 2 (LQT2), or ERG1. HERG is a voltage-activated potassium channel belonging to the eag family. Mutations in HERG can cause long QT syndrome type 2.

Nucleic acid and protein sequences for HERG are publicly available. For example, GenBank Accession Nos. NM_000238, NM_172056, NM_172057, and M<_001204798 disclose exemplary HERG nucleic acid sequences, and GenBank Accession Nos. NP_000229, NP_742053, NP_742054, and NP_001191727 disclose exemplary HERG protein sequences, all of which are incorporated by reference as present in GenBank on Oct. 15, 2011.

Nematode:

A member of the phylum Nematoda, commonly referred to as roundworms. Nematodes include free-living species (such as the soil nematode *C. elegans*) and parasitic species. Species parasitic on humans include ascarids, filarias, hookworms, pinworms, and whipworms. It is estimated that one to two billion people worldwide are infected with at least one nematode species. Parasitic nematodes also infect companion animals and livestock, including dogs and cats (e.g., *Dirofilaria immitis*; heartworm), pigs (*Trichinella spiralis*), and sheep (e.g., *Haemonchus contortus*). There are also nematode species which are parasitic on insects and plants.

Organism:

A living being or system, including unicellular organisms (such as bacteria, protozoa, or fungi) or multicellular organisms (such as nematodes, trematodes, platyhelminths, insects, non-human mammals, and humans).

III. Devices

Disclosed herein are devices (such as fluidic devices, for example, microfluidic devices) of use for recording EPGs or collecting other data (such as ion channel activity) from one or more living organisms (for example, a nematode). The devices can be configured to simultaneously collect data from multiple organisms (such as 2 or more organisms) in order to facilitate high-throughput methods. In some examples, the disclosed devices are referred to as "arrays" or "chips." These terms are used interchangeably herein.

In some embodiments, the disclosed devices include one or more inlet ports for introduction of substances to the device, for example, organisms (such as nematodes, for example, *C. elegans*), fluids (such as water, buffers, or other solutions), and/or compounds (such as drugs or test compounds). In some examples, each inlet port is connected to a single channel that delivers organisms, fluids, and/or compounds (such as drugs or test compounds) to a chamber (such as a recording channel or module). In other examples, each inlet port is connected to a series of distribution channels (for example, a series of branching channels) that distribute the organisms, fluids, and/or compounds to individual chambers (such as individual recording modules), which each receive and retain a single organism. The dimensions of the inlet port and distribution channels are such that the organisms to be tested can move through the system with fluid flow. In some embodiments, the diameter of the inlet port is approximately equal to or greater than the length of the organism. In some examples, the inlet port includes a tapered area, for example a taper from the inlet to the connection with the distribution channel network. In one example, the width and height of the distribution channels are such that the cross-sectional area is at least about 0.5× the maximum cross-sectional area of the organism when aligned with the channel. Bifurcation points of the distribution channels are flattened to prevent damage to the organisms. In a particular non-limiting example, the device accommodates adult *C. elegans* and has a port diameter of about 1.5 mm, and a channel height and width of about 50 and 100 microns, respectively.

In some examples, the organisms are retained in straight, loosely fitting channels within the recording channel by positive pressure (for example, applied by a pump connected to the inlet port). Organisms are prevented from moving further forward through the device by a trap in the form of channel whose cross-sectional area is at most about 0.15× the maximum cross-sectional area of the animal. The length of this trap is sufficient to prevent the constricted part of the organism within it to reach the far end of the trap. When recording from adult *C. elegans*, for example, the length of the trap is about 20 mm. Furthermore, the trap physically and electrically connects the recording channel to the electrode channel and thus to the organism's dedicated electrode providing, thereby, one of the two points of electrical contact with the organism. The other point of electrical contact is provided by the distribution channel connected to each recording module which, in turn, is connected to an electrode inserted into the inlet port.

The recording channel also has at least one additional opening (for example, at least one lateral opening) connected to "vent" channel, which allows fluid (for example a solution including a drug or test compound) to flow into and out of the recording module. In some examples, the fluid flows along the length of the organism, except for the part (if any) that is enclosed in the trap. In the devices disclosed herein, the electrical resistance required to observe voltage differences between the electrodes—the basis of an EPG—can be achieved without impeding the flow of fluid around the organism. In at least some examples, this precludes the use of a recording channel that fits the organism snugly all along its length. In some examples, electrical resistance is produced by close contact between the organism and the walls of funnel-shaped entrance to the trap (e.g., FIG. 1B). In some examples, such contact is achieved by the fluid pressure resulting from a pump (such as a syringe pump) connected to the inlet port. To ensure that the organism is forced into the recording module and trap, rather than into the openings to the vent channels, the joint hydraulic resistance of the vent channels (R1) is adjusted to be greater than the hydraulic resistance of the pathway consisting of the trap and electrode channel (R2). The ratio R2/R1 is a parameter that regulates two functional properties of the device, (1) the disposition of the worm in the recording channel and (2) the electrical signal to noise ratio. In the case of the first property, if this ratio is too low (for example, R2/R1 is less than about 1), the organism may be forced into one of the vent channels rather than the worm trap whereas, if this ratio is too high (for example, R2/R1 is greater than 100), the organism may be forced through the worm trap and into the electrode channel. In the case of the second property, this ratio is high enough to provide a good signal to noise ratio, but not so high as to cause the pharynx to be completely enclosed by the trap, in which case, the diffusion pathway from the recording channel to the pharynx becomes impractically long. In some examples, R2/R1 is about 1-100 (such as about 2-90, about 5-95, about 10-80, about 20-75, or about 30-50). In further examples, R2/R1 is about 1, 2, 3, 4, 5, 6, 7, 8, 9, 10, 15, 20, 25, 30, 35, 40, 45, 50, 55, 60, 65, 70, 75, 80, 85, 90, 95, 98, or 99. In one non-limiting example, the R2/R1 ratio is about 20. In some examples, the desired R2/R1 ratio is achieved by adjusting the rate of fluid flow in the device. One of ordinary skill in the art will recognize that the fluid flow rate to achieve a particular R2/R1 value depends on the overall hydraulic resistance of the device and the size and shape of the trap. In some examples, the fluid flow rate is about 1-50 μl/min (such as about 5-50, 10-40, 5-25, 20-40, or 5-10 μl/min). In other examples, the fluid flow rate is about 1, 2, 3, 4, 5, 6, 7, 8, 9, 10, 11, 12, 13, 14, 15, 20, 25, 30, 35, 40, 45, or 50 μl/min. In one non-limiting example, the rate of fluid flow is about 5-6 μl/min (for example, about 6 μl/min) for adult *C. elegans* (for example, utilizing a device as shown in FIG. 1A). The flow rate can also be adjusted empirically while the device is in use in order to have a desired length of a worm to be lodged in the trap.

In another embodiment, the organism is restrained at the confluence of the arms and stem of a Y-shaped microfluidic channel (such as the exemplary device shown in FIG. 2). The organism is inserted into the device head first. It is held at the confluence point by a vacuum-activated clamp connected to a switchable source of negative pressure such as a vacuum pump. The test solution enters via the arms of the Y, flows freely and symmetrically around the organism and exits via the stem of the Y. The confluence of the arm and stem channels is sufficiently spacious to ensure that the anterior exhibits side-to-side head movement characteristic of normal forward and backward locomotion, as well as the so-called foraging movements of the tip of the organism's head. For electrical recordings, electrodes of the type described above, are inserted into the worm inlet and the electrode port. Electrical resistance is obtained by close contact between the sides of the worm and the walls of the clamp. A video camera attached to a microscope of sufficient magnification to visualize the worm records the organism's movements at the same time as the EPG is being recorded. This arrangement provides a means of correlating changes in pharyngeal activity with changes in behavior and thereby links the EPG to conventional screening methods using behavioral endpoints.

The disclosed devices can be made from any suitable materials now known or identified in the future. In some embodiments, a device (such as a microfluidic device) is made from an elastomeric material such as a silicone polymer (for example, poly(dimethyl siloxane) (PDMS)). Suitable PDMS polymers include, but are not limited to Sylgard® 182, Sylgard® 184, and Sylgard® 186 (Dow Corning, Midland, Mich.). In one non-limiting example, the PDMS is Sylgard® 184. Additional polymers that can be used to make the disclosed devices include polyurethane, polyamides, polyethelyene, polycarbonates, polyacetylenes and polydiacetylenes, polyphosphazenes, polysiloxanes, polyolefins, polyesters (such as thermoset polyester (TPE)), polyethers, poly(ether ketones), poly(alkaline oxides), poly (ethylene terephthalate), poly(methyl methacrylate), polyurethane methacrylate (PUMA), polystyrene, thiol-enes, fluoropolymers (for example, perfluoropolyethers), Norland Optical Adhesive 81, and derivatives and block, random, radial, linear, or teleblock copolymers, cross-linkable materials such as proteinaceous materials and/or combinations of two or more thereof. Also suitable are polymers formed from monomeric alkylacrylates, alkylmethacrylates, alpha-methylstyrene, vinyl chloride and other halogen-containing monomers, maleic anhydride, acrylic acid, and acrylonitrile. Monomers can be used alone, or mixtures of different monomers can be used to form homopolymers and copolymers. See, e.g., U.S. Pat. No. 6,645,432; McDonald et al., *Electrophoresis* 21:27-30, 2000; Rolland et al., *J. Am. Chem. Soc.* 126:2322-2323, 2004; Carlborg et al., *Lab Chip* 11:3136-3147, 2011; Sollier et al., *Lab Chip* 11:3752-3765, 2011. In some examples, the channels of the device (such as a device made from PDMS) can be coated with a sol-gel.

See, e.g., Abate et al., *Lab Chip* 8:516-518, 2008. In other examples, suitable materials for making the disclosed devices include glass, ceramic, silicon, polymeric films, photoresist, hydrogels, or thermoplastic.

Microfluidic devices can be fabricated by methods known to one of ordinary skill in the art. In some examples the disclosed devices are made by molding uncured polymer from a photoresist master using standard photolithographic methods (e.g., U.S. Pat. No. 6,645,432; Madou, *Fundamentals of Microfabrication*, CRC Press, Boca Raton, Fla., 1997). In other examples, the disclosed devices are made by chemical etching, laser cutting, photopolymerization, lamination, embossing, or injection molding. In the case of glass devices, the EPG device can for instance be fabricated by etching the various types of channels into a thin glass plate, and bonding this plate to a second glass plate that serves as a flat substrate. One of ordinary skill in the art can select an appropriate fabrication method based on the selected material for the device.

The disclosed devices allow simultaneous data collection from multiple organisms, such as 1 or more (for example 2, 3, 4, 5, 6, 7, 8, 9, 10, 11, 12, 13, 14, 15, 16, 20, 24, or more) organisms, such as *C. elegans* or other nematodes or trematodes. In some embodiments, the disclosed devices accommodate up to 8 organisms (such as 1, 2, 3, 4, 5, 6, 7, or 8 organisms). The devices can be scaled up to accommodate increased numbers of organisms, such as 16, 24, 32, 40, 48, 64, 96, or more. In some examples, the device can hold 1 to 512 (such as 2-256, 8-128, 16-96 or 24-48) organisms.

In other embodiments, increased throughput is achieved by linking multiple smaller devices (such as 8 organism arrays) together. In some examples, multiple devices are linked in parallel, with each device having its own inlet port and associated electrode. In other examples, 2 or more devices, such as 8 organism arrays (such as 2, 3, 4, or more) are linked together with a common inlet port.

IV. Description of Particular Embodiments

FIG. 1A is a top view of one embodiment of the disclosed device 100, which is an exemplary 8-channel microfluidic device. The device includes an inlet port 102 including a tapered portion 103 connected to a network of worm distribution channels 104 which deliver worms and/or test solutions to eight separate recording modules 106. Each recording module is connected to an electrode channel 108. A through-hole from the top of the device into the electrode channel 108 forms an electrode port 110 into which an electrode is inserted prior to use. The electrode port 110 is of a size and shape that matches the cross-section of the electrode and forms a tight-fitting seal. In some embodiments, the electrode port is circular, but can be any shape (such as square, rectangular, oval, and so on). Each recording module is also connected to a pair of vent channels 114. Fluid flows from the inlet port 102 into the recording module 106 and exits via the vent channels 114 and/or the electrode channel 108, after which it is collected by a pair of waste reservoirs 112 and 113.

In some examples, the recording module has at least one opening (for example, at least one lateral opening) connected to a "vent" channel, which allows fluid (for example a solution including a drug or test compound) to flow out of the recording module. In some examples, the fluid flows along the length of the organism, except for the part (if any) that is enclosed in the trap. In the devices disclosed herein, the electrical seal resistance $R_s$ required to observe voltage differences between the electrodes is achieved without substantially impeding the flow of fluid around the organism. In at least some examples, this precludes the use of a recording module that fits the organism snugly all along its length. In some examples, $R_s$ on the order of 0.8 MOhm, and a signal to noise ratio (SNR) of approximately 3 in the EPG recording, can be achieved by a loose fitting channel, such as a worm channel with a width of 80 μm and a height of 50 μm. In other examples, such as when pressure is applied to the worm by means of a pump (such as a syringe pump) attached to the inlet port, $R_s$ can be as high as 7.2 MOhm, and SNR can rise to 137. In the latter example, $R_s$ is increased by close contact between the organism and the walls of funnel-shaped entrance to the trap and/or the walls of the worm trap (e.g., FIG. 1B).

Waste reservoirs can be made by forming a through-hole into which a length of tubing (for example, a 1.5 mm length of glass tubing) is inserted to increase the volume of the chamber. In some examples, the waste reservoir is about 3-6 mm in diameter and about 1-2 mm high. In one non-limiting example, the waste reservoir is about 5 mm in diameter and about 1.38 mm high. The diameter of the reservoir is constrained by the need to confine the desired number of recording modules and associated reservoirs within the allowable area of the device. For an 8-module device based on a 50 mm×75 mm substrate, the upper limit is about 6.0 mm. The lower limit of the reservoir diameter is constrained only by the amount of fluid that needs to be collected over the time course of the briefest experiment, or about 10 minutes.

A hollow electrode, through which solutions can be introduced into the device, is inserted into the inlet port after worms have been loaded. During use, all channels contain an electrically conductive solution (such as a saline solution) which provides electrical continuity between electrodes and the worm. Direction of fluid flow in the device is shown by arrows. The dimensions of each feature of an exemplary 8-channel device are given in Table 1.

TABLE 1

Dimensions of exemplary 8-channel device shown in FIG. 1A

| Feature | Length (mm) | Width (mm) | Height (mm) |
|---|---|---|---|
| Inlet port (102) | 1.50 | 1.50 | 4.00 |
| Inlet taper (103) | 7.26 | 1.50 | 0.05 |
| Worm distribution channels (104) | 31.12 | 0.10 | 0.05 |
| Electrode channel (108) | 6.50 | 0.20 | 0.05 |
| Electrode port (110) | 1.5 | 1.5 | 4.00 |
| Vent channel (112) | 20.00 | 0.10 | 0.01 |
| Waste reservoirs (113 and 114) | 5.00 | 5.00 | 4.00 |
| Worm trap (118) | 0.20 | 0.013 | 0.05 |
| Worm channel (120) | 1.97 | 0.08 | 0.05 |
| Vent channel septa (122) | 0.60 | 0.02 | 0.05 |

Figure 1B:
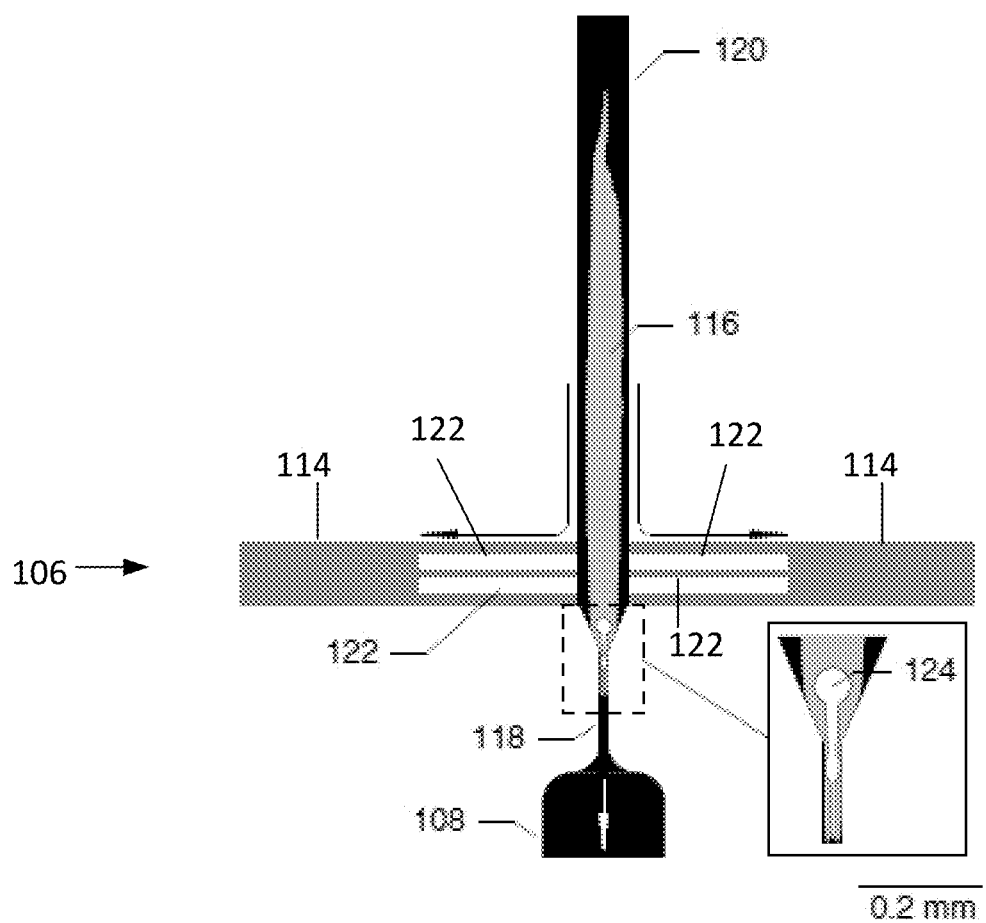
FIG. 1B is a top view showing detail of the boxed area in FIG. 1A, which is called the recording module 106. This figure shows a worm 116 in recording position in the recording module. The worm is shown resting headfirst in a worm channel 120, which includes a tight constriction (worm trap) 118, which links the worm channel 120 to the electrode channel 108. The worm is prevented from entering the vent channels 114 by vent channel septa 122, and by the fact that height of the vent channels is 10 microns whereas the height of the worm channel 120, trap 118, and electrode channel 108 is 50 microns. The area surrounded by the dashed box is expanded in the inset on the lower right. The inset shows that the worm's nose is forced into the worm trap, forming a region of high electrical resistance. The posterior half of the worm's pharynx 124 is outside the trap and therefore directly exposed to the fluid in worm channel. Direction of fluid flow is shown by arrows.
Figure 1C:
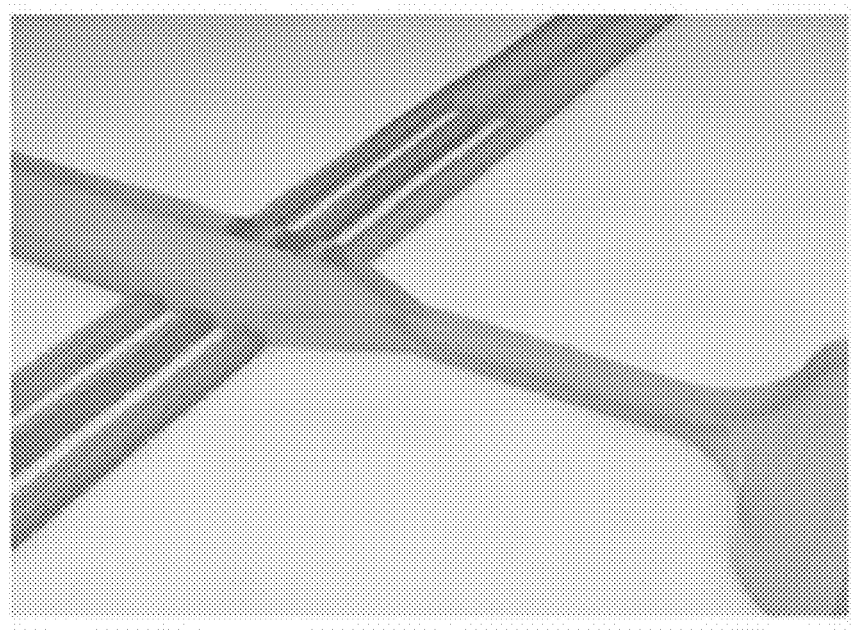
FIG. 1C is a digital image of a three-dimensional rendering of the area shown in FIG. 1B.

FIG. 1B is a top view showing detail of the boxed area in FIG. 1A, which is called the recording module 106. This figure shows a worm 116 in recording position in the recording module. The worm is shown resting headfirst in a worm channel 120, which includes a tight constriction (worm trap) 118. The worm channel 120 is linked to electrode channel 108 by means of the worm trap 118, which consists of a narrow channel that blocks the organism's forward progress through the device. The worm is prevented from entering the vent channels 114 by vent channel septa 122, and by the fact that height of the vent channels is 10 microns whereas the diameter of the worm is up to 8 times this dimension. The vent channel septa 122 are walls that rise from the substrate to the ceiling of the vent channels. The area surrounded by the dashed box is expanded in the inset on the lower right. The inset shows that the worm's nose is forced into the worm trap, forming a region of high electrical resistance. The terminal bulb of the worm's pharynx 124 is outside the trap and therefore more directly exposed to the fluid in worm channel than is the remainder of the pharynx. Direction of fluid flow is shown by arrows. FIG. 1C is a three-dimensional digital rendering of the recording module shown in FIG. 1B.

Figure 2A:
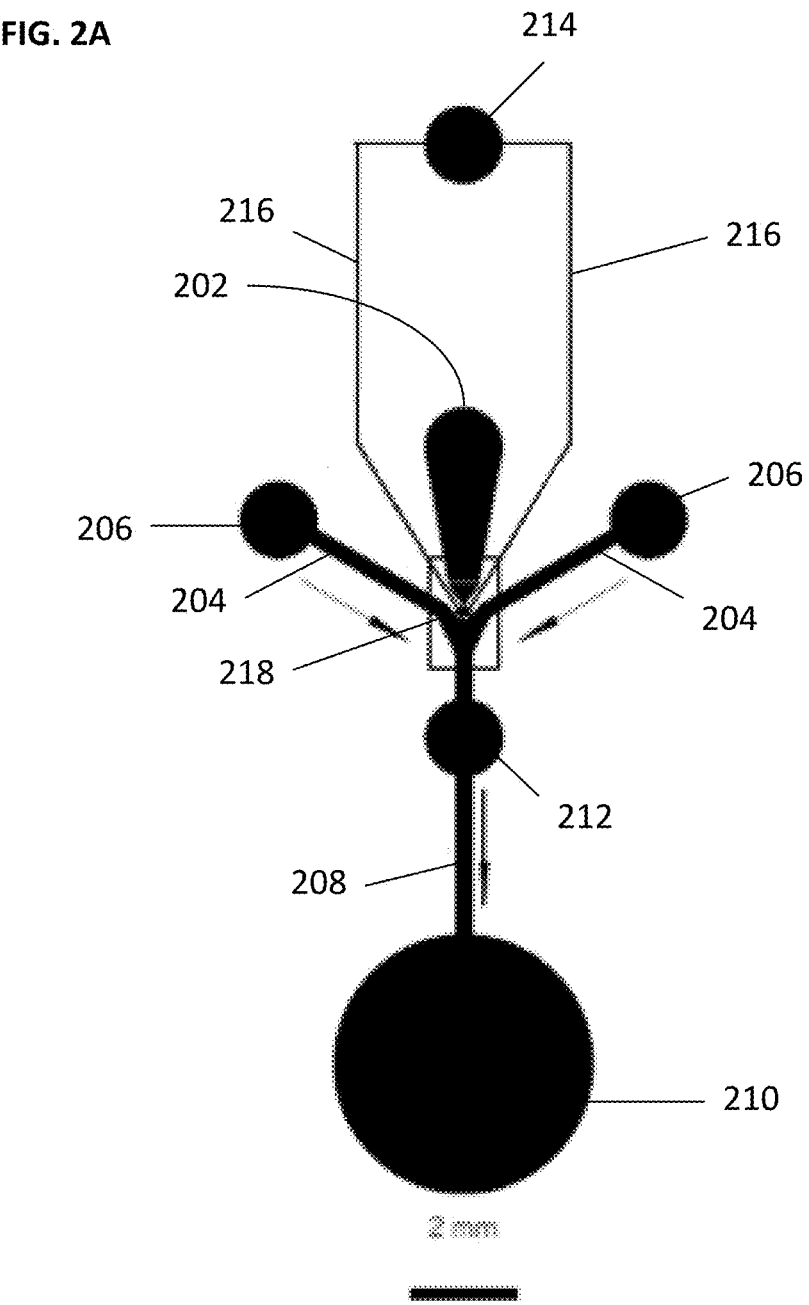
FIG. 2A is a top view of an exemplary one-channel device for applications in which pharyngeal activity is recorded electrically in conjunction with bodily movements. The device includes a worm inlet 202 connected to a Y-shaped system of channels ("arm" channels) 204. Test solution can be introduced from the two fluid inlet ports 206 and flows from the arm channels 204 through a stem channel 208 to the waste reservoir 210. For electrical recordings, cylindrical metal electrodes can be inserted into the worm inlet 202 and the electrode port 212. The device also includes a vacuum port 214 and vacuum channels 216 which activate a worm clamp 218 on application of a vacuum. Direction of fluid flow is shown by arrows.

FIG. 2A is a top view of an exemplary device for applications in which pharyngeal activity can be recorded electrically in conjunction with bodily movements. The device includes an inlet port 202 connected to a Y-shaped system of channels including arm channels 204 and a stem channel 208. Test solution can be introduced from the two fluid inlet ports 206. The solution flows down the arm channels 204 and stem channel 208 to the waste reservoir 210. For electrical recordings, electrodes can be inserted into the inlet port 202 and the electrode port 212. The device also includes a vacuum port 214 and vacuum channels 216, to which a vacuum source can be attached. Application of a vacuum activates a worm trap 218, which holds the worm at the confluence of the arm channels 204. Direction of fluid flow is shown by arrows. The dimensions of each feature of an exemplary device are given in Table 2.

TABLE 2

Dimensions of exemplary 8-channel device shown in FIG. 2A

| Feature | Length (mm) | Width (mm) | Height (mm) |
| --- | --- | --- | --- |
| Inlet port (202) | 1.50 | 1.50 | 4.00 |
| Inlet taper (203) | 7.26 | 1.50 | 0.05 |
| Arm channels (204) | 3.18 | 0.30 | 0.06 |
| Stem channels (206) | 6.80 | 0.30 | 0.06 |
| Fluid inlet ports (208) | 1.50 | 1.50 | 4.00 |
| Electrode port (212) | 1.50 | 1.50 | 4.00 |
| Waste reservoir (210) | 5.00 | 5.00 | 0.06 |
| Vacuum port (214) | 1.50 | 1.50 | 4.00 |
| Vacuum channel (216) | 10.80 | 0.06 | 0.06 |

Figure 2B:
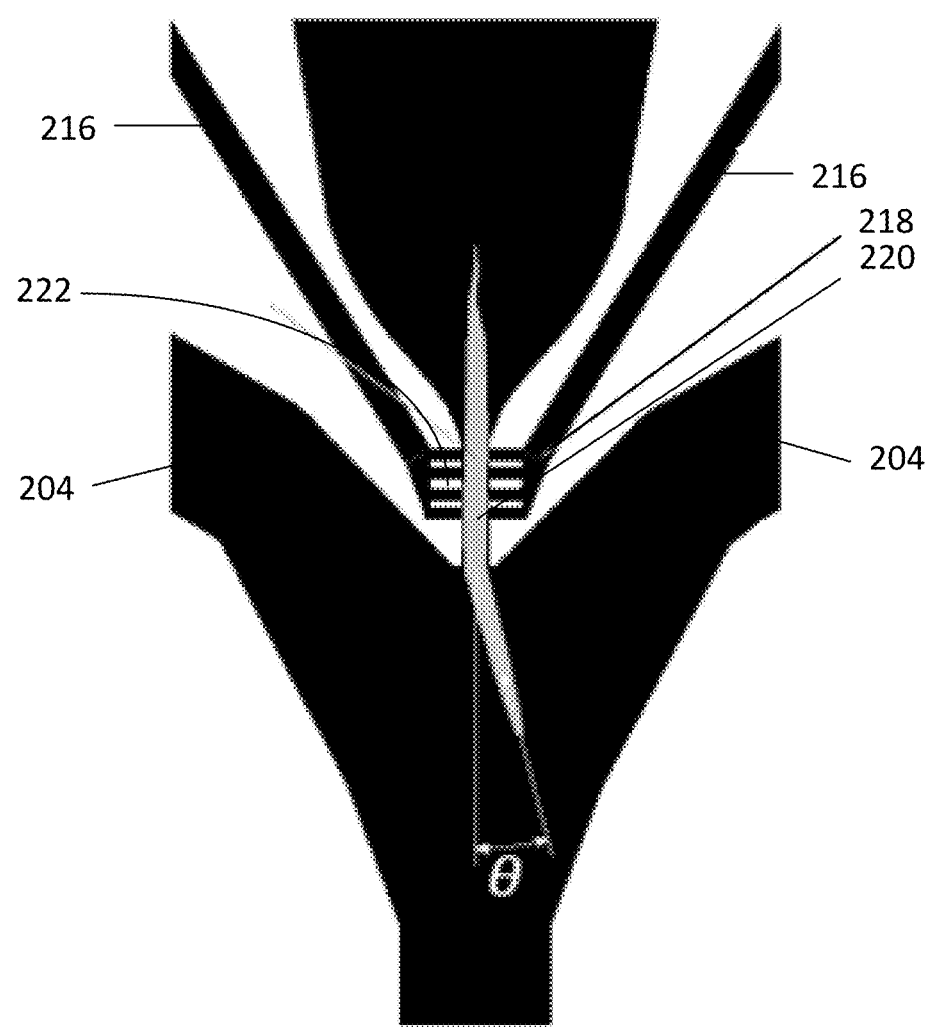
FIG. 2B is a top view showing detail of the boxed area in FIG. 2A. A worm 220 can be held by the worm clamp 218, which includes the vacuum channels 216 in contact with sides of the worm. The worm is prevented from entering the vacuum channels 216 by vacuum channel septa 222. The worm is inserted into the device headfirst and extends into the area where the arm channels 204 meet. The anterior portion of the worm remains free to move and exhibits side-to-side head movement (θ) characteristic of normal locomotion.

FIG. 2B is a top view showing detail of the boxed area in FIG. 2A. A worm 220 can be held by the worm clamp 218, which includes the vacuum channels 216 in contact with sides of the worm. The worm is held in place by application of a vacuum and is prevented from entering the vacuum channels 216 by vacuum channel septa 222. The worm is inserted into the device headfirst. The anterior portion of the worm remains free to move and exhibits side-to-side head movement (8) characteristic of normal locomotion.

In other embodiments, electrical contact with the distribution channel and the electrode channel is achieved by means of electrodes on or embedded in the surface of the substrate that forms the bottom of the recording device (such as an integrated electrode). Integrated electrodes can be included in any suitable substrate (for example, glass, PDMS, or other polymeric material). Integrated electrodes can be fabricated by any means that yields spatially patterned conductive elements that serve as wires. In one non-limiting example, the electrodes are composed of indium tin oxide. In another example, electrodes are composed of metallic silver. Patterning of electrode materials can be achieved for example, using photolithography combined with etching. If integrated electrodes are included in the device, then the electrode ports (e.g., 110 in FIG. 1A or 212 in FIG. 2A) are not required, and are eliminated in some embodiments. Worms and solutions can be introduced through the inlet port (e.g., 102 in FIG. 1A or 202 in FIG. 2A).

Waste reservoirs are not required in all embodiments of the disclosed devices. In some embodiments, the waste reservoirs (e.g., 112 and 113 in FIG. 1A or 210 in FIG. 2A) are not included in the device and waste fluid flows out the open ends of the vent channels and/or the electrode channels such that fluid released by an electrode channel never contacts fluid released by another electrode channel, or by any of the vent channels. Waste fluid is then captured by a single chamber positioned below the device such that the chamber is electrically isolated from all channels and electrodes in the device.

V. System and Data Collection

Disclosed herein are systems for data collection in whole organisms utilizing the devices described above. In some embodiments, the system includes components for recording EPGs from an organism (such as *C. elegans*). In other embodiments, the system includes components for optical imaging of an organism (such as *C. elegans*). In further embodiments, the system includes components for both EPG recording and optical imaging. In some examples, optical imaging includes visual imaging (such as observation of worm behavior). In other examples, optical imaging includes optical recording of pharyngeal activity (such as utilizing a fluorescent molecular marker of pharynx activity).

A. EPG Recordings

Disclosed herein are systems for simultaneously measuring EPG activity of two or more organisms, which include a device (or array), such as those described above. In some embodiments, the system includes the device (or array), two or more electrodes, one or more amplifiers, which are connected to outputs from each electrode, an oscilloscope, which receives input from the amplifier, a data acquisition unit, which receives input from the amplifier; and a computer, which receives input from the data acquisition unit. In some examples, the system also includes a means for regulating flow of solutions through the device (such as a pump, for example, a syringe pump). In further examples, the system also includes a microscope, which can be situated to observe the array and organisms in the array during an assay. In still further examples, the system optionally includes a vacuum pump or vacuum source for activating a worm clamp (for example, as in the device shown in FIG. 2). One of ordinary skill in the art can utilize the systems disclosed herein to measure EPG activity of organisms (such as *C. elegans*) in the array.

The organism is introduced to the device by any convenient means. In some examples, an organism (such as a *C. elegans*) is introduced into the device by transferring the organism to the inlet port (which is pre-loaded with solution) and applying gentle pressure (for example, from a syringe) to propel the organism into the distribution channels and the recording modules. In other examples, a portion of an organism (such as anterior end of a transected worm or an isolated pharynx) is introduced into the device through the inlet port. In some embodiments, the cuticle of the worm is made more permeable to drugs and test compounds by means of chemical treatments and/or genetic mutations (e.g., *C. elegans* dal-1 or bus-8 mutants). In other embodiments, the ability of the worm to capture and/or excrete foreign chemicals is compromised by genetic mutation of endogenous pumps and other proteins, including transport proteins that serve this function (e.g., pgp or mrp genes, such as *C. elegans* pgp-1 or pgp-3 mutants).

Once the device is loaded with one or more organisms (or portion(s) thereof), electrodes are inserted into the electrode ports (if required, for example if the device does not include integrated electrodes in the substrate) and one electrode (which serves as a common reference for all recording modules) is inserted in the inlet port. After insertion of electrodes (if required), the pump (such as a syringe pump) is activated. The correct disposition of the worm with respect to the worm trap occurs as a passive response to the fluid pressure supplied by the pump. In some examples, the overall flow rate through the array is such that at least a portion of the organism (for example a portion of the organism including about one-third to one-half or more of the pharynx) is forced into the smaller dimension portion of the electrode channel. In one example, about two-thirds of the length of the pharynx (for example, about 0.1 mm) is forced into the smaller dimension portion of the electrode channel, creating a tight fit between the worm and the channel. In some examples, the worm enters the channel tail first and a slightly longer portion of the worm (for example, about 0.2 mm) is forced into the channel. When the worm is in the electrode channel tail first, drug or other solutes reach the pharynx by diffusion through the cuticle in the vicinity of the pharynx and/or by ingestion of the solution by the worm. When the worm is head first in the device, drug or other solutes reach the pharynx by diffusion through the cuticle in the vicinity of the regions of the pharynx that are not enclosed in the trap. It is believed that little or no solution is available to be ingested in this case.

In one embodiment, the flow rate is such that in the absence of an organism in the chamber, the net resistance to flow in the drug channel(s) is about 20 times the resistance to flow in the electrode channel, which results in most of the flow passing through the electrode channel and lodging the organism in the electrode channel. In one embodiment, the flow rate is about 6 µl/min. The range of allowable flow rates depends on the overall hydraulic resistance from the inlet port to the waste reservoirs, and the size and shape of the trap. In the exemplary device shown in FIG. 1A and described in Table 1, the range of flow rates is approximately 5-6 µl/min.

Electrical recordings are made using standard techniques known to one of ordinary skill in the art. In some examples, EPGs are recorded by AC differential amplifiers connected to metal electrodes inserted into the device. Signals are displayed on oscilloscopes and recorded for later analysis using a data acquisition system connected to a computer running data acquisition software. Data analysis is performed offline after experiments. Raw EPG recordings can be filtered to remove slow drift and high-frequency noise. Filtered recordings can be subjected to a conventional peak-finding algorithm to aid in determining EPG frequency as a function of time over a rolling time window. The peak-finding algorithm can also be used to measure inter-spike intervals or peak amplitudes, and to make histograms of these quantities as a function of time or experimental treatments, including drugs, mutants, and toxic compounds. In other examples, the instantaneous root-mean-square (RMS) of the signal is calculated after subtracting an estimate of the electrical noise associated with each channel.

B. Optical Methods

Also disclosed herein are systems for both recording an EPG and optically imaging one or more organisms. In some embodiments, the system includes a device (or array) described above. In some embodiments, the system includes the device (or array) and a microscope, such as a fluorescence microscope.

The devices disclosed herein can be adapted for optical recordings of pharyngeal activity. In some examples, the device is bonded to a standard cover glass, of the type used for mounting tissue samples on microscope slides. The device is then mounted in metal frame and animals are introduced as described above. The frame containing the device is placed on the stage of a compound microscope. Pharyngeal activity is recorded from above or below the chip, depending on the type of microscope used (standard or inverted). In some examples, optical images are obtained simultaneously or substantially simultaneously with EPG recording. In other examples, optical imaging and EPG recording are sequential. Optical imaging and EPG recording can occur in either order. In some embodiments, EPG recordings are obtained as described in section V(A), above.

In some examples, optical imaging is utilized to observe the behavior of an organism (such as a *C. elegans*). For example, the organism can be exposed to a compound and the response (such as frequency, duration, and/or direction of movement) is observed. In particular examples, a vacuum is applied to draw the worm's cuticle into vacuum channels (for example, as in the exemplary device shown in FIGS. 2A and B) creating a tight seal between the worm and the walls and septa of the vacuum channels. The electrical resistance in the Y-chip is thus independent of the rate of flow of solution through the device. In some embodiments, such as the Y-shaped device described above, the anterior portion of the worm remains free to move and exhibits side-to-side head movement ($\theta$) characteristic of normal locomotion. These movements are recorded by a video camera attached to a macro lens or stereomicroscope that views the worm from above. Video recordings of worm behavior (for example, 30 frames/sec) are analyzed by a computer program that computes head angle $\theta$ in each image. Briefly, frames are first masked and thresholded to obtain an image of the worm. The centerline of the worm is then obtained by a skeletonization procedure. Starting at the position of the restraint, the centerline is traversed to find the tip of the head, defined as the point furthest from the restraint.

In other examples, cellular or molecular activity is observed by optical imaging (such as fluorescent imaging). In one non-limiting example, a *C. elegans* expressing a fluorescent calcium sensing molecule (for example G-CaMP; Nakai et al., *Nat. Biotechnol.* 19:137-141, 2001) is observed with optical imaging. The worm is exposed to a compound and the fluorescence of cells expressing the calcium sensing molecule is observed. In some embodiments, the optical imaging is recorded as a video file. In other examples, the optical imaging is recorded as a photograph or digital image.

VI. Methods of Screening

The devices and methods disclosed herein can be used to identify potentially useful compounds (such as therapeutics, for example anthelmintic drugs) or potentially harmful or toxic compounds (such as compounds that block HERG channels or environmental toxins). In some examples, the disclosed devices and methods allow rapid and cost-effective screening, including high-throughput screening embodiments.

A. Identification of Therapeutic Compounds

Disclosed herein are methods for identifying compounds of interest, such as therapeutic compounds, utilizing the devices and systems disclosed herein. In some embodiments, the disclosed methods include screening for anthelmintic or antimicrobial compounds. In other embodiments, the methods include screening for compounds of use for treating neuromuscular diseases (such as muscular dystrophies, for example, Duchenne muscular dystrophy), neurodegenerative diseases (such as Alzheimer disease, Parkinson disease, Huntington disease, or tauopathies), mitochondrial disorders, or substance abuse disorders.

Methods of screening for or identifying anthelmintic compounds include introducing nematodes (such as *C. elegans*) in a device described herein, contacting the nematode with one or more test compounds, and recording an EPG from the nematode, as described above. The EPG in the presence of the one or more test compounds is compared to a control (such as an EPG from the same or a different *C. elegans* in the absence of the test compounds) and the compound is identified as an anthelmintic or candidate anthelmintic if the EPG is altered (for example, the size and/or frequency of the EPG, or a portion thereof is decreased) in the presence of the test compound as compared to the control. In some examples, the nematodes are contacted with serotonin or bacterial food prior to and/or concurrent with the test compound to stimulate pharyngeal pumping.

In some examples, the methods include determining a dose-response curve of a test compound in a nematode and comparing the dose-response curve of the compound to a control. In some examples, the control is a dose-response curve of a known anthelmintic (for example, ivermectin, levamisole, paraherquamide, emodepside, or piperazine) in a wild type nematode and the compound is identified as an anthelmintic or a candidate anthelmintic if the dose-response curve is shifted to the left compared to the control. In other examples, the control is a dose-response curve of a known anthelmintic (for example, ivermectin, levamisole, paraherquamide, emodepside, or piperazine) in a resistance mutant nematode and the compound is identified as an anthelmintic or a candidate anthelmintic if the dose-response curve is shifted to the right compared to the control.

Methods of screening for or identifying compounds of potential use for treating disease, such as neurodegenerative disease (for example, Parkinson disease, Huntington disease, Alzheimer disease), neuromuscular disease (for example, spinal muscular atrophies or amyotrophic lateral sclerosis), and muscular degenerative disease (for example, muscular dystrophies or sarcopenia) and/or inhibiting or reducing aging include introducing nematodes (such as *C. elegans*) in a device described herein, contacting the nematode with one or more test compounds, and recording an EPG from the nematode, as described above. In some examples, such as for diseases for which the *C. elegans* genome contains a gene that is orthologous to the human gene implicated in the disease, a strain is created or obtained in which that gene is mutated and is utilized in the screening methods. Otherwise, a strain is created in which the human gene is expressed in *C. elegans* by transgenic techniques. Such a strain is considered to be a valid disease model if one or more aspects of its phenotype are consistent with the mechanisms or manifestations of the disease. Strains that are disease models can be used in drug screens by searching for compounds that mitigate one or more of these phenotypes in *C. elegans*. This mitigation can be the result of either chronic or acute exposure to a test compound. In one example, the EPG array is used to test for mitigation of disease phenotypes consisting of alterations in the behavior, physiology, and/or other aspects of the pharynx. In one non-limiting example, the *C. elegans* model for spinal muscular atrophy (SMA) exhibits reduced rates of pharyngeal pumping. A candidate compound in a drug screen for SMA is identified by a reduction or reversal of the reduced pumping phenotype as compared to a control (such as an untreated *C. elegans*). In other examples, histograms of interspike intervals are used to assess effects of treatments on pumping. In the case of some *C. elegans* disease models, the presence or absence of a pharyngeal phenotype is unknown. In these examples, the EPG array is used to test for such a phenotype. If a pharyngeal phenotype exists, then the model can be used as above to screen for drugs. Some controls in drug screening experiments would be to apply the test compound to wild type nematodes with the expectation that changes in the pharyngeal phenotype are absent, or in a direction opposite to the change seen in the disease model. For example, a drug effective against SMA might have no effect on wild type worms, or it might increase the rate of pharyngeal pumping.

*C. elegans* is well-established as a model in aging research. The devices disclosed herein provide a means of assessing or screening the effects of treatments (for example, genetic alterations, pharmaceutical compounds, and/or environmental conditions) on the process, extent and mechanism of aging. The *C. elegans* pharynx exhibits a decline in pumping rate with increasing age. In some examples, the EPG devices are used to quantify the effects of treatments on aging. This is done by growing and maintaining worms under conditions of chronic exposure to the treatment and sampling pumping rate throughout the aging process by monitoring pumping rate in an EPG device. Pumping is stimulated by contact with serotonin or bacterial food. In some examples, controls include worms of similar ages that were not exposed the treatment.

Many nematode species are parasites of plants (see, e.g. online at nematode.unl.edu/agripests.htm), causing an estimated $100 billion of worldwide crop losses annually. These nematodes also transmit damaging viruses to plants. Available control measures are very limited, with most plant nematicides withdrawn from the market because of environmental concerns. Many species of plant nematodes have an elaborate feeding apparatus, including a sharp stylet that is rhythmically protruded and retracted to pierce plant cell walls and pump fluids during feeding (Wyss, *Feeding behavior of plant parasitic nematodes* In "The Biology of Nematodes, D. L. Lee, editor, 2002, Taylor and Francis, London). When plant nematodes are contacted with serotonin, this feeding apparatus, which is homologous to the pharynx of non-plant nematodes, emits electrical impulses that can be monitored by conventional EPG recording methods (Rolfe and Perry, *Nematology* 3:31-34, 2001). Many plant nematodes are of a size that is compatible with microfluidic devices. Thus, also disclosed herein are methods of assessing or screening the effects of treatments (for example, genetic alterations, pharmaceutical or other compounds, and/or environmental conditions) on plant nematodes utilizing the devices disclosed herein. In some examples, the EPG devices are used to quantify the effects of treatments on feeding in plant nematodes. Pumping is stimulated by contact with serotonin in the device. The nematodes are exposed to the treatment chronically or acutely. In some examples, pumping rate is measured. In other examples, histograms of interspike intervals are used to assess effects of treatments on pumping. Controls include worms of the same species and age that are not exposed to the treatment, for instance.

After nematodes, the most abundant parasitic worms are digenetic trematodes, also known as flukes or flatworms. They parasitize a broad range of vertebrates, including humans and domestic animals, leading to disease and economic losses. Whereas nematodes have a complete digestive system, with a mouth at one end and an anus at the other, a fluke's mouth leads to a blind sac. However, like nematodes, many flukes have well-developed pharynges, which are used to ingest blood or tissue from hosts. Many species of parasitic and free-living flukes have been the subjects of intense biological inquiry in laboratory settings. As is the case for *C. elegans*, studies of free-living species can inform research on parasitic species. The muscular pharynx is typically richly innervated by neurons containing various neurotransmitters and neuromodulators. For example, dopamine, allatostatin, and octopamine receptors are present in the neural plexus innervating the pharynx of the non-parasitic freshwater flatworm *Schmidtea mediterranea*. In some examples, the EPG devices disclosed herein are used to quantify the effects of drugs and other treatments on feeding in trematodes. Trematodes are introduced into an EPG array that has been modified by adjusting the size of the channels to accommodate them. Pharyngeal activity is stimulated by contacting the animals with an appropriate neurotransmitter. The nematodes are exposed to the treatment chronically or acutely. In some examples, pumping rate is measured. In other examples, histograms of interspike intervals are used to assess effects of treatments on pumping. Controls involve trematodes of the same species and age that are not exposed to the treatment, for instance.

B. Identification of Compounds with Toxicity

Also disclosed herein are methods of identifying compounds that are toxic or have toxic effects on an organism. In some embodiments, the methods include screening compounds for inhibitors of the HERG channel (for example, potentially cardiotoxic compounds). In other embodiments, the methods include screening compounds for toxicity, for example potential environmental toxicity.

Inhibition of the HERG potassium channel can cause long QT syndrome and potentially fatal ventricular arrhythmias. Several compounds have been withdrawn from late stage clinical trials as a result of cardiotoxicity due to HERG channel inhibition and screening for long QT effects is now mandatory for new drug candidates. Therefore, methods to identify potential HERG channel inhibitors early in drug development can eliminate potentially unsafe compounds prior to significant investment and can streamline development of compounds that do not exhibit cardiotoxicity.

In some examples, methods of identifying compounds that inhibit the HERG channel include introducing nematodes (such as *C. elegans*) in a device described herein, contacting the nematode with one or more test compounds, and recording an EPG from the nematode, as described above. The EPG in the presence of the one or more test compounds is compared to a control (such as an EPG from the same or a different *C. elegans* in the absence of the test compound) and the compound is identified as an inhibitor of HERG if the EPG is altered (for example, inhibited) in the presence of the test compound as compared to the control. In some examples, the EPG is inhibited (for example, the size and/or frequency of the EPG, or a portion thereof is decreased) in the presence of the test compound as compared to the control. In some examples, the separation between the E and R spikes of the individual action potentials that comprise EPG is increased, indicating reduced HERG channel function. In other examples, the amplitude of the E and R spikes is reduced. In still other examples, the frequency of action potentials within the EPG is increased or reduced indicating, respectively, facilitation or inhibition of the EPG. In some examples, the nematodes are contacted with serotonin or bacterial food prior to and/or concurrent with the test compound to stimulate pharyngeal pumping.

In other examples, the methods include introducing a nematode expressing HERG (for example, by genetic knock-in) in a device described herein, contacting the nematode with one or more test compounds, and recording an EPG from the nematode, as described above. In some examples, the nematode includes a deletion or mutation of the HERG ortholog exp-2. The EPG in the presence of the one or more test compounds is compared to a control (such as an EPG from the same or a different *C. elegans* in the absence of the test compound) and the compound is identified as an inhibitor of HERG if the EPG is altered (for example, inhibited) in the presence of the test compound as compared to the control. In some examples, the EPG is inhibited (for example, the size and/or frequency of the EPG, or a portion thereof is decreased) in the presence of the test compound as compared to the control. In some examples, the separation between the E and R spikes of the individual action potentials that comprise EPG is increased, indicating reduced HERG channel function. In other examples, the amplitude of the E and R spikes is reduced. In still other examples, the frequency of action potentials within the EPG is increased or reduced indicating, respectively, facilitation or inhibition of the EPG. In some examples, the nematodes are contacted with serotonin prior to and/or concurrent with the test compound to stimulate pharyngeal pumping.

Methods of screening for or identifying toxic compounds include introducing nematodes (such as *C. elegans*) in a device described herein, contacting the nematode with one or more test compounds, and recording an EPG from the nematode, as described above. The EPG in the presence of the one or more test compounds is compared to a control (such as an EPG from the same or a different *C. elegans* in the absence of the test compound) and the compound is identified as toxic or potentially toxic if the EPG is altered (for example, inhibited) in the presence of the test compound as compared to the control. In some examples, the amplitude of action potentials or frequency of action potentials is decreased in the presence of the test compound as compared to the control. In other examples, changes in interspike intervals of the EPG are assessed. In some examples, the nematodes are contacted with serotonin or bacterial food prior to and/or concurrent with the test compound to stimulate pharyngeal pumping. In some examples, the compound is an environmental toxin (such as a heavy metal), pesticide, herbicide, industrial chemical, or naturally occurring compound of interest. Exemplary compounds include, but are not limited to, those listed in the 1989 OSHA Toxic and Hazardous Substances List or online at bioinformatics.charite.de/supertoxic/.

C. Test Compounds

The methods disclosed herein are of use for identifying compounds that can be useful as drugs (for example, anthelmintic compounds) or compounds that exhibit toxic effects (such as HERG channel blockers). A "compound" or "test compound" is any substance or any combination of substances that is useful for achieving an end or result. In some examples, the compounds identified using the methods disclosed herein can be of use as anthelmintics or other types of drugs, for example by altering (for example inhibiting) *C. elegans* EPG activity. In other examples, the compounds identified using the methods disclosed herein are identified as toxic, for example inhibiting HERG channel activity. Any compound that has potential (whether or not ultimately realized) to affect EPG activity, HERG activity, or other characteristics can be tested using the methods of this disclosure.

Exemplary compounds include, but are not limited to, peptides, such as soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.*, 37:487-493, 1991; Houghten et al., *Nature*, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA*, 90:6909-6913, 1993), vinylogous polypeptides (Hagihara et al., *J. Am. Chem. Soc.*, 114:6568, 1992), nonpeptidal peptidomimetics with glucose scaffolding (Hirschmann et al., *J. Am. Chem. Soc.*, 114:9217-9218, 1992), analogous organic syntheses of small compound libraries (Chen et al., *J. Am. Chem. Soc.*, 116:2661, 1994), oligocarbamates (Cho et al., *Science*, 261:1303, 1003), and/or peptidyl phosphonates (Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.*, 14:309-314, 1996; PCT App. No. PCT/US96/10287), carbohydrate libraries (see, e.g., Liang et al., *Science*, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525, 735 and 5,519,134; morpholino compounds, U.S. Pat. No. 5,506,337; benzodiazepines, U.S. Pat. No. 5,288,514) and the like.

Libraries useful for the disclosed screening methods can be produced in a variety of manners including, but not limited to, spatially arrayed multipin peptide synthesis (Geysen, et al., *Proc. Natl. Acad. Sci.*, 81(13):3998-4002, 1984), "tea bag" peptide synthesis (Houghten, *Proc. Natl. Acad. Sci.*, 82(15):5131-5135, 1985), phage display (Scott and Smith, *Science*, 249:386-390, 1990), spot or disc synthesis (Dittrich et al., *Bioorg. Med. Chem. Lett.*, 8(17):2351-2356, 1998), or split and mix solid phase synthesis on beads (Furka et al., *Int. J. Pept. Protein Res.*, 37(6):487-493, 1991; Lam et al., *Chem. Rev.*, 97(2):411-448, 1997). Libraries useful for the disclosed methods can also be included in solution, for example in defined pools of compounds. Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential therapeutic compounds. Such combinatorial libraries are then screened in one or more assays as described herein to identify those library members (particularly chemical species or subclasses) that display a desired characteristic activity (such as altering, for example altering (e.g., inhibiting) EPG or HERG channel activity), and compounds that display one or more desired characteristics are identified and/or selected.

The compounds identified using the methods disclosed herein can serve as conventional "lead compounds" or can themselves be used as potential or actual therapeutics. In some instances, pools of candidate agents may be identified and further screened to determine which individual or sub-pools of agents in the collective have a desired activity.

The present disclosure is illustrated by the following non-limiting Examples

Example 1

Simultaneous Recording of EPG from Multiple *C. elegans* with Microfluidic Arrays This example demonstrates simultaneous measurement of EPGs from multiple *C. elegans* in a microfluidic array.

Methods

Nematodes:

*C. elegans* strains were grown on Nematode Growth Medium (NGM) agar plates seeded with the $OP_{50}$ strain of *E. coli*. All strains were obtained from the Caenorhabditis Genetics Center (CGC; Minneapolis, Minn.). Wild-type worms were Bristol N2 and Ivermectin (IVM) resistant mutants were DA1316 avr-14(ad1302); avr-15(ad1051); glc-1(pk54). Worms were age synchronized by allowing gravid adults to lay eggs on seeded NGM plates for approximately 6 hr. The adults were then removed and embryos allowed to develop to adulthood at room temperature.

Fabrication of Devices:

Devices were fabricated using standard soft lithographic methods (Qin et al., *Nat. Protoc.* 2010; 5(3):491-502). A silicon wafer master for the chemosensory device was created by exposing a 55 µm layer of SU-8 2050 resist (Microchem, Newton, Mass.) through a transparency mask and dissolving away unexposed material. Masters were replica molded in Polydimethylsiloxane (PDMS, Dow Corning Sylgard® 184, Corning, N.Y.). Masters were treated with chlorotrimethylsilane (Sigma-Aldrich, St. Louis, Mo.) to prevent adhesion of PDMS to the master. Holes for ports, inlets, and fluid reservoirs were formed using biopsy punches of the appropriate diameter (ports and inlets, 1.5 mm; reservoirs, 5 mm). PDMS castings were bonded to glass substrates after 30 sec exposure to an oxidizing air plasma. After bonding, the capacity of each fluid reservoir was increased by inserting a 1.5 cm length of 5 mm glass tubing.

Solutions:

All experiments utilized M9 buffer (recipe available on the World Wide Web at 130.15.90.245/wormlab_recipe_book.htm#Commonlab; containing $KH_2PO_4$, $NaHPO_4$, NaCl and $MgSO_4$) to which serotonin (5HT) was added to stimulate pharyngeal pumping (Raizen and Avery, *Neuron* 1994 March; 12(3):483-95). Stocks of serotonin creatine sulfate monohydrate (Sigma H7752; St. Louis, Mo.) were prepared in M9 buffer at 40 mM and held in small aliquots at −20° C. until use. Each day of an experiment, a fresh aliquot was thawed and diluted to 10 mM 5HT in M9 buffer. This "M9-5HT" buffer was the control medium to which drugs or other compounds were added. Stock solutions of ivermectin (10 mM; Sigma 8898) were made up in dimethyl sulfoxide (DMSO, Fisher D-136; Fair Lawn, N.J.) and held at −20° C. for no longer than 2 wk. On the day of an experiment, IVM was diluted to the final concentration in M9-5HT buffer containing 0.005% Fast Green (Fisher F-99) as a visual indicator of drug flow within the chip (see below). The dye-containing M9-5HT buffer was filtered (PALL Life Sciences 25 mm Acrodisc syringe filter with 0.2 µm HT Tuffryn Membrane; Port Washington, N.Y.) before drug or DMSO was added.

Loading Worms into the Device:

Young adult worms were transferred from growth plates into a glass well containing M9-5HT buffer and left to acclimate for 10 minutes. While viewed under transillumination on a Stemi SV6 binocular stereomicroscope (Carl Zeiss Inc., Thornwood, N.Y.), 8 worms were picked using a loop tool and placed into the inlet port of the device, which had been preloaded with M9-5HT buffer. A 10 cc syringe filled with M9-5HT buffer connected to a length of 1.5 mm polyethylene tubing was then inserted into the inlet port and gentle pressure was applied to propel worms into the eight individual worm channels in the device. The tubing connected to the inlet port was then removed and loaded chip moved to the EPG recording apparatus.

Solution Delivery:

Solutions were delivered at a rate of 6 µl/min via a syringe pump (Harvard Apparatus PHD 2000; Holliston, Mass.) driving a pair of 3 mL syringes. One syringe was filled with M9-5HT buffer and the other with buffer to which vehicle, or drug plus vehicle, was added. Each syringe was fitted with a 25 gauge stub needle connected to the 25 gauge tubing of a reference electrode (see above) by a 30 cm length of fine polyethylene tubing (BPE-T25, Instech Solomon, Plymouth Meeting, Pa., USA). Solution changes were effected by removing the reference electrode connected to the first syringe and inserting the reference electrode connected to the second syringe. This procedure eliminated potential cross-contamination between solutions. The latency between insertion of the electrode and arrival of the solution at the worm's location, defined by the change in solution color, was approximately 60 sec.

Electrophysiological Recordings:

EPGs were recorded by a pair of 4-channel AC differential amplifiers (A-M Systems model 1700, Carlsborg, Wash.) connected to electrodes inserted into the device. Electrodes were made from 0.5 inch long passivated 17 gauge stainless steel tubes (0.058 inch OD, 0.0475 inch ID, New England Small Tube, Litchfield, N.H.). One electrode, located in the fluid inlet port, served as a common reference for all 8 recordings. This electrode contained a 1.0 inch length of 25 gauge stainless steel hypodermic tubing for solution delivery, held in place by a 0.5 inch length of heat shrink tubing. The reference electrode was connected to the negative input of each amplifier channel. The other electrodes were inserted into the individual electrode ports associated with each of the 8 worms (see FIG. 1A) and connected to the positive inputs of the amplifiers. Recordings were made at gains of 1000× or 10,000× and filtered with a low-pass cutoff of 1.0 Hz and a high-pass cutoff of 5 kHz. Signals were further conditioned by a 60 Hz notch filter.

Signals were displayed on a pair of four channel oscilloscopes (TDS 2024B, Tektronix, Beaverton, Oreg.) at a sweep rate sufficient to resolve the components of individual pharyngeal action potentials. Signals were recorded for later analysis using a data acquisition system (Micro1401-3, Cambridge Electronic Design, Cambridge, UK) connected to a computer running Spike2 software (version 7.06a, Cambridge Electronic Design, Cambridge, UK). Data were sampled at 10 kHz per channel. An additional channel was used as a keystroke-controlled event marker (e.g., time of drug delivery).

Data Acquisition and Analysis:

Data were acquired continuously in Spike 2 from when electrodes were inserted into the chip until an experiment was terminated (generally 1-2 h after drug addition). For long recording sessions (e.g., overnight), Spike2 was set to acquire short data segments at regular intervals (e.g., 5 min of recording every 20 min, sampled at 5 kHz per channel). At the end of each experiment, the original 9-channel data file was saved and also split into 8 individual files, each consisting of one worm recording and its associated event markers. These files were used for subsequent quantitative analysis.

Figure 3:
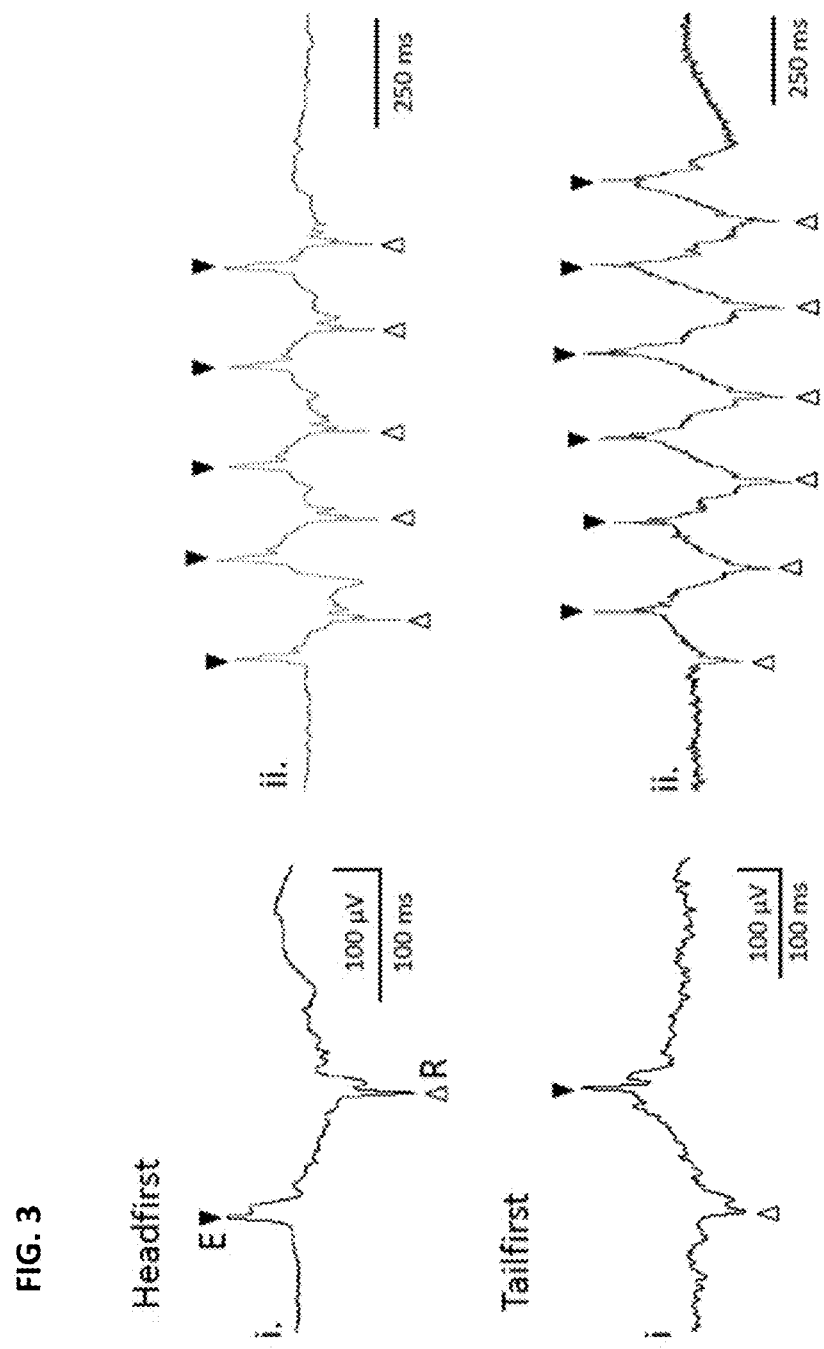
FIG. 3 is a set of EPG recordings from a *C. elegans* oriented "headfirst" in the recording module of the 8-channel device (top) and from a *C. elegans* oriented "tailfirst" in the recording module of the 8-channel device (bottom). For each, part i (left) shows a single pharyngeal contraction expanded to show detail and part ii (right) shows a series of contractions from the *C. elegans*. Filled triangles (E), excitatory phase of pharyngeal contraction; open triangles (R), relaxation phase of pharyngeal contraction. By convention, EPG events are displayed in the headfirst recording configuration. EPG signals in the tailfirst configuration are largely a mirror image of the headfirst signal. Vertical scale bars refer to both parts i and ii.

Raw EPG recordings were filtered to remove slow drift and high-frequency noise. Filtered recordings were subjected to a conventional peak-finding algorithm to aid in determining EPG frequency as a function of time over a rolling time window. The peak-finding algorithm was also used to measure interspike intervals or peak amplitudes, and to make histograms of these quantities as a function of time or experimental treatments, including drugs, mutants, and toxic compounds. In other examples, the instantaneous root-mean-square (RMS) of the signal was calculated after subtracting an estimate of the electrical noise associated with each channel Results EPGs were recorded simultaneously from individual worms utilizing a device described herein. The success rate for loading worms into channels was 96% (worms in 289 of 301 channels, in 37 chips). The EPGs can be recorded regardless of whether the *C. elegans* enter the recording chamber head first or tail first. EPGs recorded from the "tail first" configuration have the opposite polarity and are mirror images of "head first" recordings. FIG. 3 shows exemplary EPG traces recorded from a "head first" *C. elegans* and a "tail first" *C. elegans*.

Figure 4A:
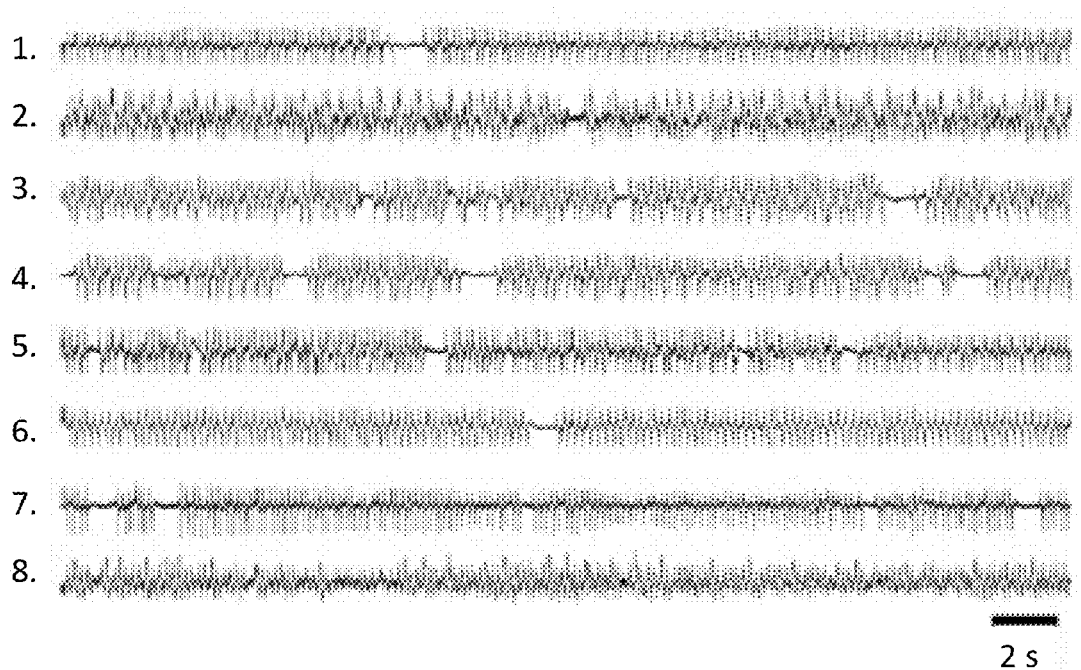
FIGS. 4A and B are EPG traces simultaneously recorded from eight *C. elegans* (labeled 1 to 8) in a microfluidic EPG array.
Figure 4B:
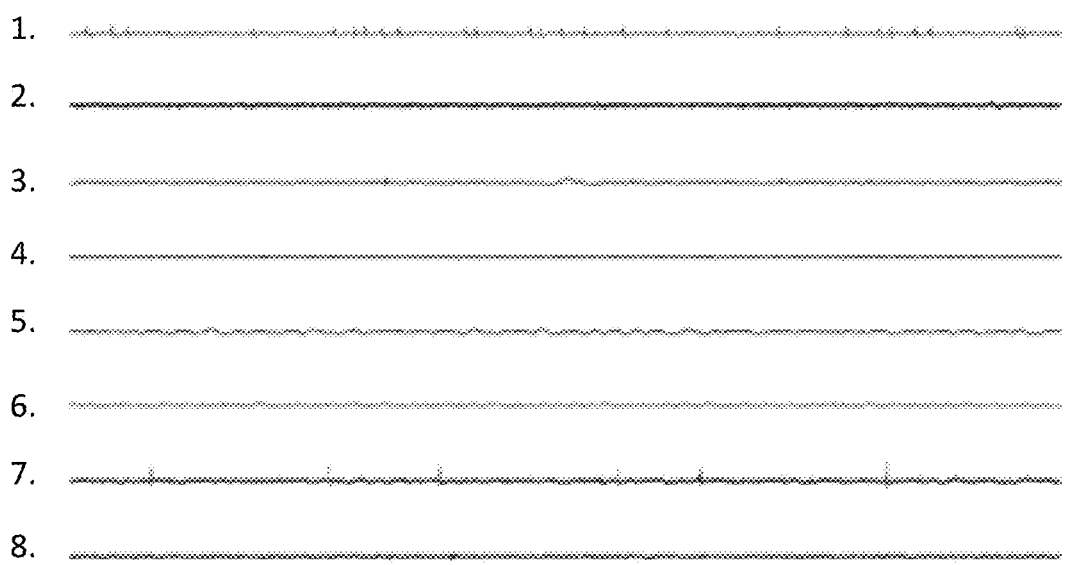
FIG. 4B is a set of EPG traces from the same worms 10 minutes after initiating perfusion of 10 µM ivermectin in M9-5HT buffer (with 0.1% DMSO). Voltage gains were the same as in FIG. 4A. All worms except 2 and 8 were oriented headfirst in the channels.
Figure 5A:
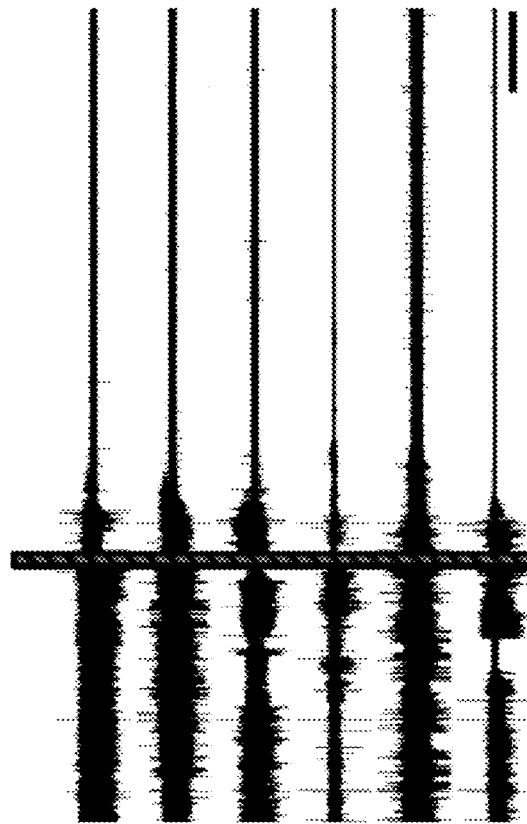
FIGS. 5A and B are sets of EPG traces simultaneously recorded from six wild type N2 *C. elegans* (FIG. 5A) and six ivermectin-resistant mutant *C. elegans*, of genotype avr-14 (ad1302); avr-15(ad1051); glc-1(pk54) (FIG. 5B) in a microfluidic EPG array. Worms were perfused with M9-5HT buffer and then switched to perfusion in M9-HT buffer with 10 µM ivermectin (indicated by vertical bar).
Figure 5B:
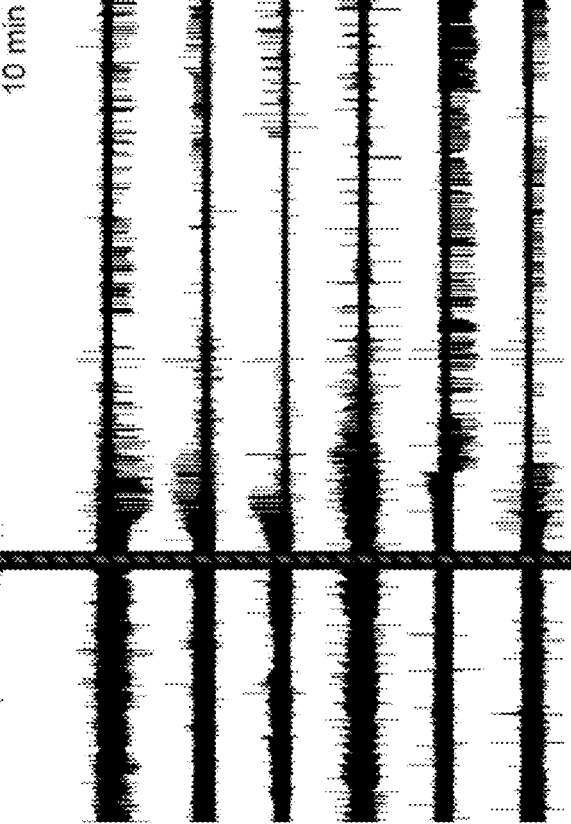

FIG. 4 shows simultaneous EPG recordings from eight *C. elegans* at baseline and 10 minutes after treatment with 10 µM ivermectin. Treatment with ivermectin significantly reduced or even eliminated the size and frequency of EPG signal in all eight *C. elegans*. However, ivermectin failed to block pharyngeal pumping in the ivermectin resistance mutant avr-14(ad1302); avr-15(ad1051); glc-1(pk54) (FIG. 5). This also demonstrates that the EPG recordings are stable over hours-long periods of time.

Figure 6A:
FIGS. 6A-C is a set of three EPG recordings from the same *C. elegans*.
Figure 6B:
Figure 6C:

The effect of levamisole on *C. elegans* EPG recorded using the chip was also investigated. Levamisole is a nicotinic receptor agonist that causes body wall muscle paralysis. The receptors for levamisole are not present in the pharynx. As shown in FIG. 6, treatment of *C. elegans* with 10 mM levamisole completely inhibited pharyngeal pumping within 10 minutes (FIG. 6B), demonstrating that anthelmintic activity of test compounds having extra-pharyngeal sites of action can be determined using the disclosed chips and methods. In addition, the drug could be effectively washed out and pharyngeal pumping returned to normal within 60 minutes of wash onset (FIG. 6C).

Example 2

Comparison of Microfluidic EPG Recording with Conventional EPG Recording

This example provides a comparison of EPG recordings from *C. elegans* utilizing the devices and methods disclosed herein with conventional EPG recordings and other microfluidic methods.

Figure 8B:
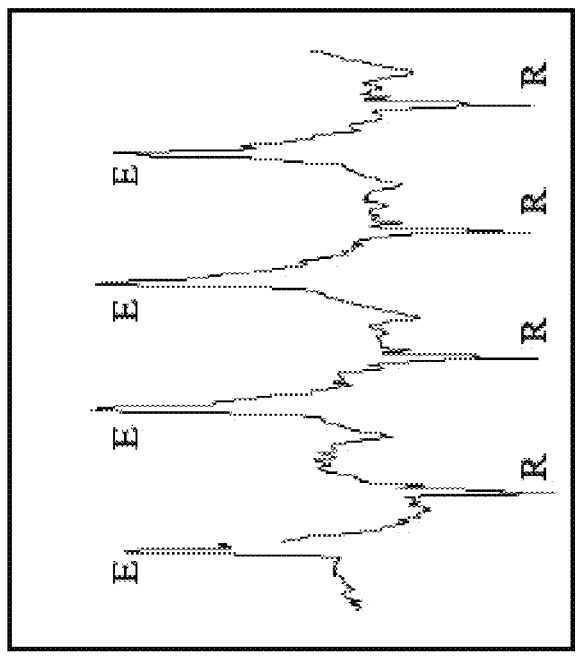
FIGS. 8A and B are a pair of EPG traces in *C. elegans* obtained by conventional patch clamp method (FIG. 8A) or a microfluidic device as disclosed herein (FIG. 8B). Four successive pharyngeal pumping events are shown. E, excitation phase; R, relaxation phase.
Figure 8A:
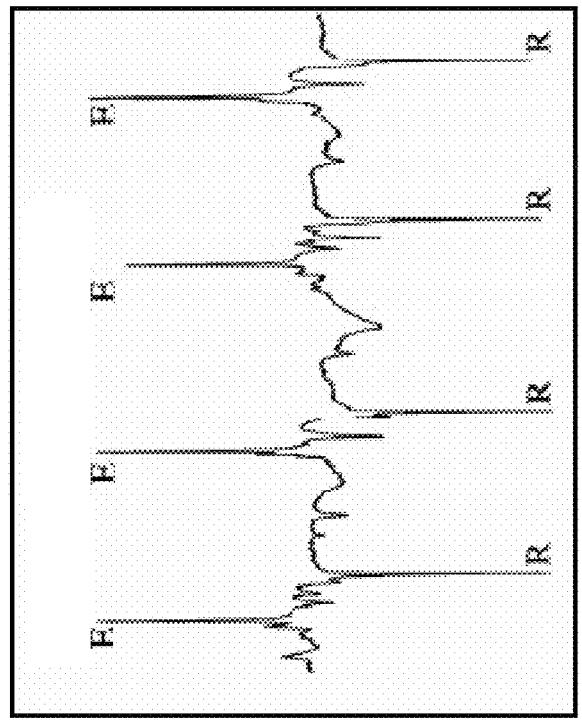

An EPG from a wild type worm obtained by the conventional patch clamp method is shown in FIG. 8A (from Davis et al., *J. Neurosci.* 15:8408-8418, 1995). FIG. 8B shows an EPG from a wild type worm obtained as described in Example 1.

Figure 9B:
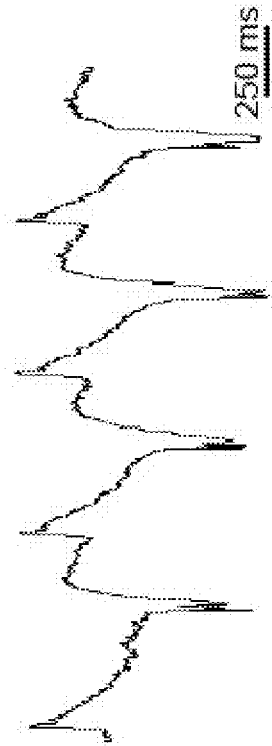
FIG. 9B shows an EPG from a wild type worm positioned in the EPG array with a perfusion rate of 50 µl/min (top). This produces a "tight" fit of the worm in the recording module where the distal portion of the worm is forced into the worm trap (bottom).
Figure 9B:
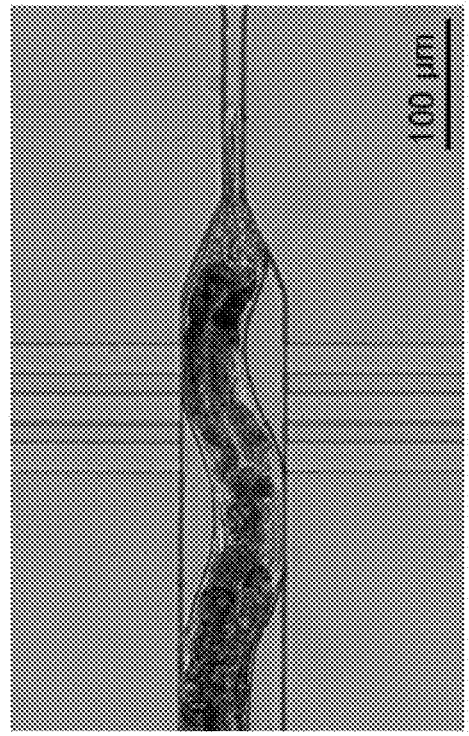
Figure 9A:
FIGS. 9A and B show EPGs from two wild types *C. elegans*.
Figure 9A:
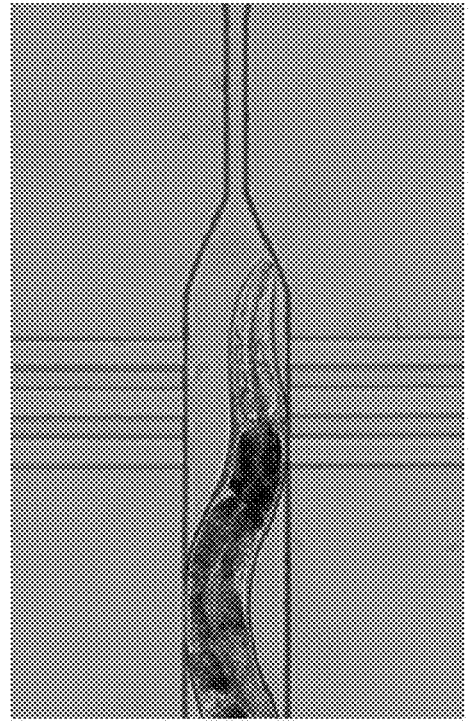

FIG. 9A shows an EPG from a wild type worm positioned in the EPG array without activation of the syringe pump ("loose" fit). The signal to noise ratio was 3.3 in this condition. FIG. 9B shows an EPG from a wild type worm positioned in the EPG array with a perfusion rate of 50 µl/min. This caused the distal portion of the worm to be forced into the worm trap (a "tight" fit). In this condition, the signal to noise ratio was 41.8, a 12-fold improvement over the "loose" fit recording.

The methods disclosed herein increased the signal to noise ratio of the EPG compared to conventional EPG or distributed resistance EPG methods. The disclosed methods also improved the waveform of the EPG, making it much more like what is seen in conventional EPG recordings (via the glass electrode method). Without being bound by theory, it is believed that this improvement in waveform results from compressing the electrical resistance across which the voltage is measured into a very small length of the channel. The waveform of the EPG in the distributed resistance method was distorted by the fact that the resistance is distributed all along the length of the worm.

Example 3

Characterization of Mode of Action of Anthelmintics by Microfluidic EPG Recording This example describes methods for characterizing the mode of action of anthelmintic compounds utilizing EPG recordings from *C. elegans* in a microfluidic EPG array.

Known anthelmintic compounds are classified into at least five groups based on their mechanism of action. *C. elegans* resistance mutants in which the target of particular anthelmintics has been eliminated by genetic mutation have been generated. The anthelmintic classes, representative drugs, and *C. elegans* resistance mutants are shown in Table 3.

TABLE 3

Key modes of action of anthelmintic drugs and respective resistance mutants

| Mode of Action | Representative Drug | Resistance Mutations |
| --- | --- | --- |
| Nicotinic AChR agonist | Levamisole | ric-3, unc-63, oig-1 |
| Glutamate gated chloride channel agonist | Ivermectin | avr-14, avr-15, glc-1 |
| Nicotinic AChR antagonist | Paraherquamide | ric-3, unc-63, oig-1 |
| SLO-1 potassium channel activator | Emodepside | slo-1 (js118) |
| GABA receptor agonist | Piperazine | unc-49 (e407) |

Elimination of a drug's molecular target by mutation abolishes the specific action of the drug, leaving only its non-specific effects, thereby shifting the dose-response curve towards higher concentrations. Therefore, the classification of an unknown drug can be determined by identifying the resistance mutant(s) for which the unknown drug shifts the dose-response curve.

EPG dose-response curves are obtained for each drug shown in Table 1 using wild type *C. elegans* and one or more resistance mutant strains shown in Table 1, utilizing the methods described in Example 1. Dose response curves are then obtained for a panel of test compounds (for example, other known anthelmintics or candidate anthelmintic compounds) in wild type and the resistance mutant *C. elegans*. Test compounds which shift at least one dose response curve to the right are identified as candidate anthelmintics and the mode of action is determined based on the resistance mutants affected.

Example 4

Methods of Identifying Anthelmintic Compounds

This example describes particular methods that can be used to identify anthelmintic compounds. One of ordinary skill in the art will appreciate that methods that deviate from these specific methods can also be used to successfully identify anthelmintic compounds.

*C. elegans* are injected into an 8-channel array and their insertion into the electrode channel of the array is monitored using a light microscope. *C. elegans* are contacted with a solution containing serotonin and baseline EPGs are recorded. The same *C. elegans* are then contacted with a solution including serotonin and one or more test compounds. EPGs are recorded from the *C. elegans* for a period of time. The size, frequency, and waveform of the EPGs are monitored and compared to a control (such as the baseline EPG or a reference EPG). A compound that decreases size or frequency of the EPG or alters the waveform of the EPG is identified as a candidate anthelmintic drug.

Example 5

Methods of Identifying HERG Channel Blockers

This example describes particular methods that can be used to identify HERG channel blockers. One of ordinary skill in the art will appreciate that methods that deviate from these specific methods can also be used to successfully identify HERG channel blockers.

*C. elegans* that have a genetic knockout of the exp-2 gene and knockin of the HERG gene are injected into an 8-channel array and their insertion into the electrode channel of the array is monitored using a light microscope. *C. elegans* are contacted with serotonin and baseline EPGs are recorded from the *C. elegans*. The *C. elegans* are then contacted with a solution including serotonin and one or more test compounds. EPGs are recorded from the *C. elegans* for a period of time. The size, frequency, and waveform of the EPGs are monitored and compared to a control (such as the baseline EPG or a reference EPG). A compound that decreases size or frequency of the EPG or alters the waveform of the EPG is identified as a candidate HERG channel blocker with potential cardiotoxicity.

Example 6

Optical Imaging of *C. elegans* Pharynx Activity

A genetically encoded calcium indicator, G-CaMP (Nakai et al., *Nat. Biotechnol.* 19:137-141, 2001), was expressed under control of the myo-2 promoter, which is specific for pharyngeal muscle. Worms were restrained in so-called artificial soil (Lockery et al., *J. Neurophysiol.* 99:3136-3143, 2008), a type of microfluidic device, placed feature side down on a glass coverslip. Pumping was induced by adding 10 mM serotonin to the saline solution bathing the worm. The device containing the worm was placed on the stage of an inverted compound microscope (Ziess Axiovert 135), illuminated with light in the wavelength band of 436±10 nm, and viewed with a 63× oil immersion objective. A video camera (ORCA-AG, Hamamatsu, Japan) recorded images in the emission band 535±40 nm. The frame rate was 25 fps and the exposure time was 40 msec. Fluorescence intensity was measured within a region of interest that contained all labeled muscle cells.

Figures 7A, 7B:
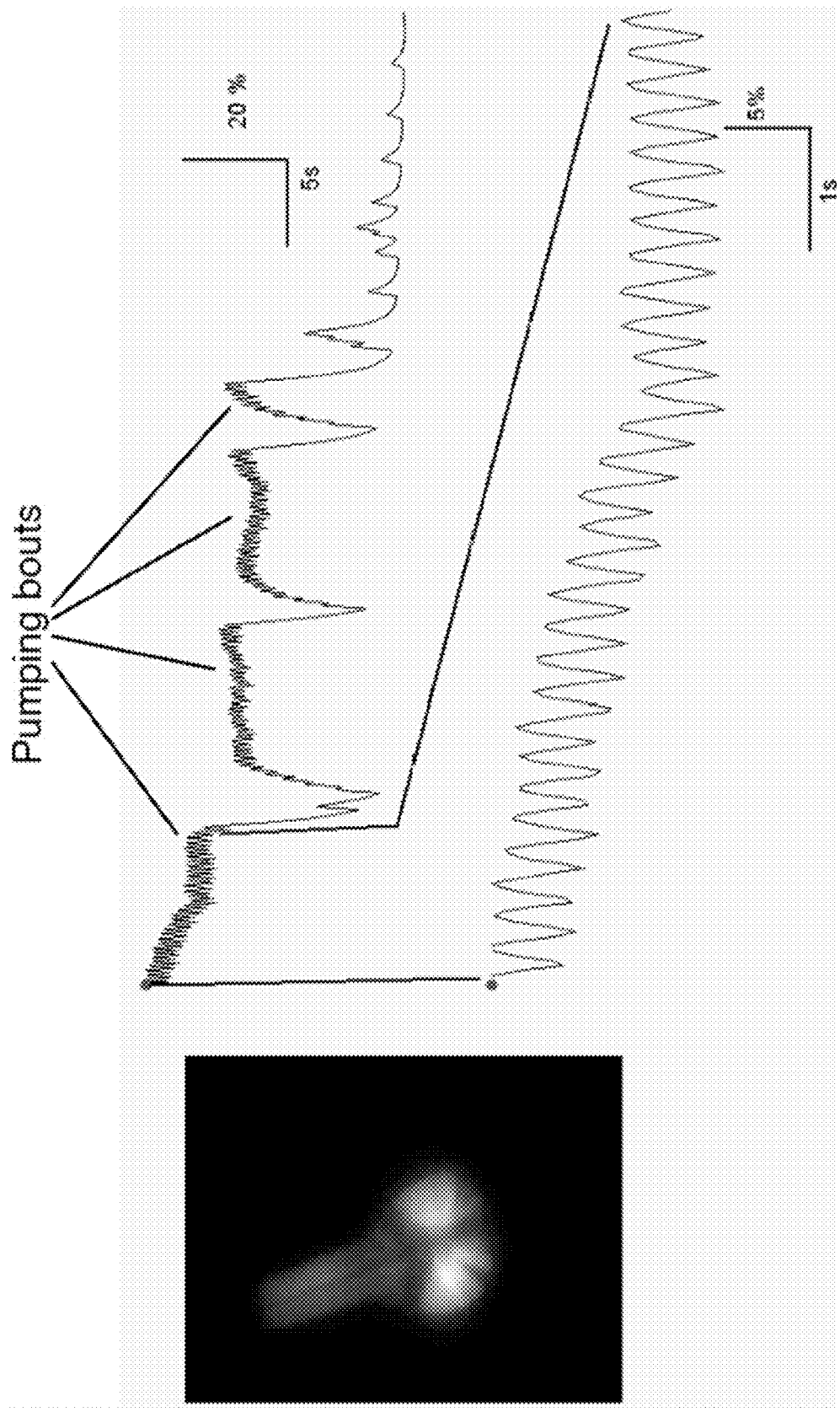
FIGS. 7A and B show optical recording of pharyngeal pumping obtained from an individual *C. elegans* restrained in a microfluidic device.
FIG. 7B shows traces of fluorescence as a function of time. The upper trace shows the percent change in fluorescence as a function of time. The lower trace is an expanded view of the first bout of pumping, showing fluctuations in fluorescence that correspond to individual pumping events.

FIG. 7 depicts an optical recording of pharyngeal pumping obtained from a worm restrained in a microfluidic device. The muscle cells of terminal bulb of the pharynx, and two additional muscle cells express G-CaMP (FIG. 7A). The intensity of G-CaMP fluorescence increases with increasing calcium concentration. Calcium concentration is a reliable proxy for electrical activity in muscles. FIG. 7B shows the percent change in fluorescence as a function of time (top). Intracellular calcium concentration rises and remains high during sustained bouts of pumping, and falls during toward baseline values when pumping stops. The lower trace (FIG. 7B) is an expanded view of the first bout of pumping, showing fluctuations in fluorescence that corresponded to individual pumping events.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A microfluidic device for recording an electropharyngeogram (EPG) from at least one whole nematode, comprising:
    an inlet port;
    a distribution channel, wherein a first end of the distribution channel is connected to the inlet port;
    a chamber for immobilizing the at least one nematode, wherein a second end of the distribution channel is connected to the chamber;
    two or more integrated electrodes;
    one or more recording amplifiers connected to outputs from the two or more integrated electrodes; and
    an outlet connected to the chamber, wherein the distribution channel and chamber have a rectangular cross-section.

2. The device of claim 1, wherein the device comprises a silicone polymer.

3. The device of claim 2, wherein the silicone polymer comprises poly(dimethyl siloxane).

4. The device of claim 1, wherein the at least one nematode is *Caenorhabditis elegans*.

5. A method of recording an electropharyngeogram (EPG) from at least one whole nematode, comprising:
    introducing at least one nematode in the device of claim 1 through the inlet port;
    subjecting the at least one nematode to conditions sufficient to cause a portion of the at least one nematode to be drawn into the chamber; and
    recording electrophysiological signals from the at least one nematode, thereby recording an EPG.

6. The method of claim 5, wherein the conditions sufficient to cause a portion of the at least one nematode to be drawn into the chamber comprises applying a vacuum or positive pressure to the device.

7. The method of claim 5, wherein the at least one nematode is a *Caenorhabditis elegans* or a parasitic nematode species.

8. The method of claim 5, further comprising:
    contacting the at least one nematode with one or more test compounds;
    recording an EPG from the at least one nematode;
    determining whether the EPG from the at least one nematode is altered as compared to a control; and
    identifying a test compound as a compound for treating disease or reducing aging, an anthelmintic compound or a cardiotoxic compound if the EPG recorded from the at least one nematode contacted with the test compound is altered as compared to the control.

9. The method of claim 8, further comprising contacting the at least one nematode with serotonin, bacterial food, or saline prior to or concurrent with the one or more test compounds.

10. The method of claim 8, wherein determining whether the EPG is altered comprises determining the frequency of the EPG, amplitude of the EPG, the EPG waveform, inter-spike interval, or a combination thereof.

11. The method of claim 8, wherein the at least one nematode comprises *Caenorhabditis elegans* or a parasitic nematode species.

12. The device of claim 1, further comprising at least one waste reservoir.

13. The device of claim 1, further comprising an oscilloscope, wherein the oscilloscope receives input from the one or more recording amplifiers.

14. The device of claim 1, wherein the one or more recording amplifiers connected to outputs from the two or more integrated electrodes are one or more differential amplifiers.

15. The method of claim 11, wherein the *C. elegans* expresses a human gene.

16. The method of claim 15, wherein the *C. elegans* expresses human ether-a-go-go related potassium channel (HERG).

17. The method of claim 16, wherein the *C. elegans* further comprises a genetic knockout of exp-2.

* * * * *